United States Patent
Golnabi et al.

(10) Patent No.: US 8,977,340 B2
(45) Date of Patent: Mar. 10, 2015

(54) SYSTEM AND METHOD FOR COLLECTION AND USE OF MAGNETIC RESONANCE DATA AND MICROWAVE DATA TO IDENTIFY BOUNDARIES OF INTEREST

(75) Inventors: Amir H. Golnabi, Hanover, NH (US); Keith D. Paulsen, Hanover, NH (US); Paul M. Meaney, Hanover, NH (US)

(73) Assignee: Dartmounth College, Hanover, NH (US)

(*) Notice: Subject to any disclaimer, the term of this patent is extended or adjusted under 35 U.S.C. 154(b) by 124 days.

(21) Appl. No.: 13/577,788
(22) PCT Filed: Feb. 9, 2011
(86) PCT No.: PCT/US2011/024216
§ 371 (c)(1), (2), (4) Date: Sep. 14, 2012
(87) PCT Pub. No.: WO2011/100343
PCT Pub. Date: Aug. 18, 2011

(65) Prior Publication Data
US 2013/0204118 A1 Aug. 8, 2013

Related U.S. Application Data

(60) Provisional application No. 61/302,758, filed on Feb. 9, 2010.

(51) Int. Cl.
*A61B 5/055* (2006.01)
*A61B 5/00* (2006.01)
(Continued)

(52) U.S. Cl.
CPC ............ *A61B 5/0035* (2013.01); *G06T 7/0012* (2013.01); *A61B 5/0059* (2013.01);
(Continued)

(58) Field of Classification Search
USPC .......... 600/410, 411, 427, 430; 324/306, 307, 324/309, 315
See application file for complete search history.

(56) References Cited

U.S. PATENT DOCUMENTS

| 5,841,288 A | 11/1998 | Meaney et al. |
| 6,061,589 A | 5/2000 | Bridges et al. |

(Continued)

FOREIGN PATENT DOCUMENTS

| WO | 2004052169 A2 | 6/2004 |
| WO | 2006069195 A3 | 6/2006 |
| WO | WO2011/100343 A3 | 8/2011 |

OTHER PUBLICATIONS

Amir H. Golnabi, Paul M. Meaney, Shireen D. Gelmer, Margaret W. Fanning, Keith D. Paulsen; "Microwave Imaging Utilizing a Soft Prior Constraint", Medical Imaging 2009: Biomedical Applications in Molecular, Structural, and Functional Imaging; Proc. of SPIE vol. 7262 72622L-1; Downloaded from SPIE Digital Library on Oct. 7, 2009.

(Continued)

*Primary Examiner* — Michael Rozanski
(74) *Attorney, Agent, or Firm* — Peter A. Nieves; Sheehan Phinney + Green PA

(57) ABSTRACT

A system and method for detecting permittivity and conductivity boundaries within a high resolution spatial image of a material is presented. Electrical properties of a material, such as permittivity and conductivity, may assist in identification of physical properties of the material. Structural boundaries within tissue may be identified in spatial images, such as MR images. Image reconstruction algorithms may combine these structural boundaries with microwave images of the tissue to determine the permittivity and conductivity parameters within the structural boundaries. In the case of soft tissue, the microwave images may be captured simultaneously with the spatial images. The microwave images may be taken at a different time from the spatial image for rigid tissue. The method may be employed for two dimensional or three dimensional image reconstruction.

15 Claims, 21 Drawing Sheets

(51) Int. Cl.
    *A61B 6/03* (2006.01)
    *G06T 7/00* (2006.01)
    *A61B 5/05* (2006.01)
(52) U.S. Cl.
    CPC .............. *A61B 5/055* (2013.01); *A61B 5/4312* (2013.01); *A61B 6/032* (2013.01); *A61B 5/0507* (2013.01); *G06T 2207/10081* (2013.01); *G06T 2207/10088* (2013.01); *G06T 2207/30068* (2013.01)
    USPC ........................... 600/411; 600/427; 600/430

(56) References Cited

U.S. PATENT DOCUMENTS

| | | | |
|---|---|---|---|
| 6,198,834 | B1 | 3/2001 | Belk et al. |
| 6,421,550 | B1 | 7/2002 | Bridges et al. |
| 6,448,788 | B1 | 9/2002 | Meaney et al. |
| 6,865,494 | B2 | 3/2005 | Duensing et al. |
| 6,879,735 | B1 | 4/2005 | Portniaguine et al. |
| 7,164,105 | B2 | 1/2007 | Godshalk et al. |
| 7,169,107 | B2 | 1/2007 | Jersey-Willuhn et al. |
| 7,257,244 | B2 | 8/2007 | Miga |
| 7,319,212 | B2 | 1/2008 | Godshalk et al. |
| 7,327,822 | B2 | 2/2008 | Sauer et al. |
| 7,439,736 | B2 | 10/2008 | Meaney et al. |
| 2004/0077943 | A1 | 4/2004 | Meaney et al. |
| 2004/0167399 | A1 | 8/2004 | Li |
| 2005/0203387 | A1 | 9/2005 | Godshalk et al. |
| 2005/0270220 | A1 | 12/2005 | Baharav et al. |
| 2006/0012367 | A1 | 1/2006 | Meaney et al. |
| 2006/0058606 | A1 | 3/2006 | Davis et al. |
| 2006/0241410 | A1 | 10/2006 | Fang et al. |
| 2007/0015993 | A1 | 1/2007 | Ciocan et al. |
| 2007/0039950 | A1 | 2/2007 | Godshalk et al. |
| 2007/0210077 | A1 | 9/2007 | Godshalk et al. |
| 2009/0036766 | A1 | 2/2009 | Meaney et al. |

OTHER PUBLICATIONS

P. M. Meaney, A. Golnabi, M. W. Fanning; S. D. Geimer, K. D. Paulsen; "Dielectric Volume Measurements for Biomedical Applications", Antenna Technology and Applied Electromagnetics and the Canadian Radio Science Meeting, 2009, ANTEM/URSI 2009. 13th International Symposium on; Feb. 15-18, 2009.

Emil Y. Sidky, Xiaochuan Pan,y Ingrid S. Reiser, Robert M. Nishikawa, Richard H. Moore and Daniel B. Kopans; "Enhanced imaging of microcalcications in digital breast tomosynthesis through improved image-reconstruction algorithms" Apr. 7, 2009; arXiv:0904.1016v1 ]physics.med-ph] Apr. 7, 2009.

I. Reiser, J. Bian, R. M. Nishikawa, E. Y. Sidky, and X. Pan; "Comparison of reconstruction algorithms for digital breast tomosynthesis"; arXiv:0908.2510v1 [physics.med-ph] Aug. 18, 2009.

Nadine Joachimowicz, Jordi J. Mallorqui, Jean-Charles Bolomey, and Antoni Broquetas; "Convergence and Stability Assessment of Newton-Kantorovich Reconstruction Algorithms for Microwave Tomography", IEEE Transactions on Medical Imaging, vol. 17, No. 4, Aug. 1998, pp. 562-570.

Sangeetha Somayajula, Anand Rangarajan and Richard M. Leahy; "PET Image Reconstruction using Anatomical Information Through Mutual Information Based Priors: A Scale Space Approach"; Biomedical Imaging: From Nano to Macro, 2007. ISBI 2007. 4th IEEE International Symposium on, Apr. 12-15, 2007.

Ioannis T. Rekanos and Theodoros D. Tsiboukis; "A Finite Element-Based Technique for Microwave Imaging of Two-Dimensional Objects", IEEE Transactions on Instrumentation and Measurement, vol. 49, No. 2, Apr. 2000, pp. 234-239.

Emil Y Sidky; Ingrid Reiser; Robert M. Nishikawa, Xiaochuan Pan, Rick Chartrand, Daniel B Kopans and Richard H Moore; "Practical iterative image reconstruction in digital breast tomosynthesis by non-convex TpV optimization"; From Conference vol. 6913 Medical Imaging 2008: Physics of Medical Imaging, Feb. 16, 2008.

Sangeetha Somayajula, Ewen Asma, and Richard M. Leahy; "PET Image Reconstruction using Anatomical Information through Mutual Information Based Priors" 2005 IEEE Nuclear Science Symposium Conference Record, pp. 2722-2726.

P. M. Meaney, M. W. Fanning, Q. Fang, K. D. Paulsen; Initial Experience With a Microwave Imaging System for Monitoring Temperature Change in an Animal Model; Papers from 23rd Annual International Conference of the IEEE Engineering in Medicine and Biology Society, Oct. 25-28, 2001; held in Istanbul,Turkey.

Hamid Dehghani, Ph.D.; Three Dimensional Reconstruction Algorithm for Imaging Pathophysiological Signals within Breast tissue using Near Infrared Light; Dartmouth College, Hanover, NH 03755 Jul. 2005.

Paul M. Meaney, Margaret W. Fanning, Timothy Raynolds, Colleen J. Fox, Qianqian Fang, Christine A. Kogel, Steven P. Poplack, and Keith D. Paulsen; Initial Clinical Experience with Microwave Breast Imaging in Women with Normal Mammography; Published in final edited form as: Acad Radiol. Feb. 2007 ; 14(2): 207-218.

Paul M. Meaney, Keith D. Paulsen, Brian W. Pogue, and Michael I. Miga; Microwave Image Reconstruction Utilizing Log-Magnitude and Unwrapped Phase to Improve High-Contrast Object Recovery, IEEE Transactions on Medical Imaging, vol. 20, No. 2, Feb. 2001, pp. 104-116.

International Preliminary Examination Report for PCT/US03/30577; dated Mar. 1, 2005.

Anand Rangarajan, Ing-Tsung Hsiao, and Gene Gindi; "A Bayesian Joint Mixture Framework for the Integration of Anatomical Information in Functional Image Reconstruction", Dec. 30, 1998, Journal of Mathematical Imaging and Vision; vol. 12.

Wolfgang Bangerth, Amit Joshi; "Adaptive finite element methods for the solution of inverse problems in optical tomography", 2008 Inverse Problems 24 034011.

S. Benameur, M.Mignotte, J.Meunier, and J.-P. Soucy; "Image Restoration Using Functional and Anatomical Information Fusion with Application to SPECT-MRI Images"; Hindawi Publishing Corporation, International Journal of Biomedical Imaging, vol. 2009; Article ID 843160, 12 pages.

Adam M. Alessio, Paul E. Kinahan, and Thomas K. Lewllen; "Improved Quantitation for PET/CT Image Reconstruction with System Modeling and Anatomical Priors", Med Phys. Nov. 2006;33(11):4095-103.

Gindi G, Lee M, Rangarajan A, Zubal IG; "Bayesian reconstruction of functional images using anatomical information as priors", IEEE Trans Med Imaging. 1993;12(4):670-80.

Jovan G. Brankov; Yongyi Yang, Richard M. Leahy*, and Miles N. Wernick; Multi-Modality Tomographic Image Reconstruction Using Mesh Modeling, Biomedical Imaging, 2002. Proceedings. 2002 IEEE International Symposium on.

Qi Shan, Jiaya Jia, Aseem Agarwala; "High-Quality Motion Deblurring from a Single Image"; ACM Transactions on Graphics, vol. 27, No. 3, Article 73, Publication date: Aug. 2008.

Phan T. H. Truc, Sungyoung Lee, and Tae-Seong Kim; "A Density Distance Augmented Chan-Vese Active Contour for CT Bone Segmentation,"; Conf Proc IEEE Eng Med Biol Soc. 2008.

Ouyang X, Wong WH, Johnson VE, Hu X, Chen CT., "Incorporation of correlated structural images in PET image reconstruction"; IEEE Trans Med Imaging. 1994; 13(4):627-40.

Lee, Mindy; "Bayesian reconstruction in Emission Tomography Using Gibbs Priors", Dissertation presented to the Faculty of the Graduate School of Yale University, May 1994.

A. Rangarajan, I. T. Hsiao and G. Gindi; "Integrating Anatomical Priors in ECT Reconstruction via Joint Mixtures and Mutual Information"; Nuclear Science Symoposium, 1998. Conference Record. 1998 IEEE (vol. 3), pp. 1584-1588.

Qianqian Fang, Stefan A. Carp, Juliette Selb, Greg Boverman, Quan Zhang, Daniel B. Kopans, Richard H, Moore, Eric L. Miller, Dana H. Brooks, and David A. Boas; "Combined Optical Imaging and Mammography of the Healthy Breast: Optical Contrast Derived from Breast Structure and Compression"; IEEE Trans Med Imaging. Jan. 2009; 28(1): 30-42, doi:10.1109/TMI.2008.925082.

(56) References Cited

OTHER PUBLICATIONS

Dominique Van de Sompela and Michael Brady; "Simultaneous Reconstruction and Segmentation Algorithm for Digital Breast Tomosynthesis"; Biomedical Imaging: From Nano to Macro, 2008. ISBI 2008. 5th IEEE International Symposium on; May 14-17, 2008; pp. 1035-1038.

Ben Brooksby, Shudong Jiang, Hamid Dehghani, Brian W. Pogue, Keith D. Paulsen, Christine Kogel, Marvin Doyley, John B. Weaver, Steven P. Poplack; "Magnetic resonance-guided near-infrared tomography of the breast." (publ. Nov. 2004); Dartmouth College/Medical School; Review of Scientific Instruments vol. 75, No. 12, Dec. 2004.

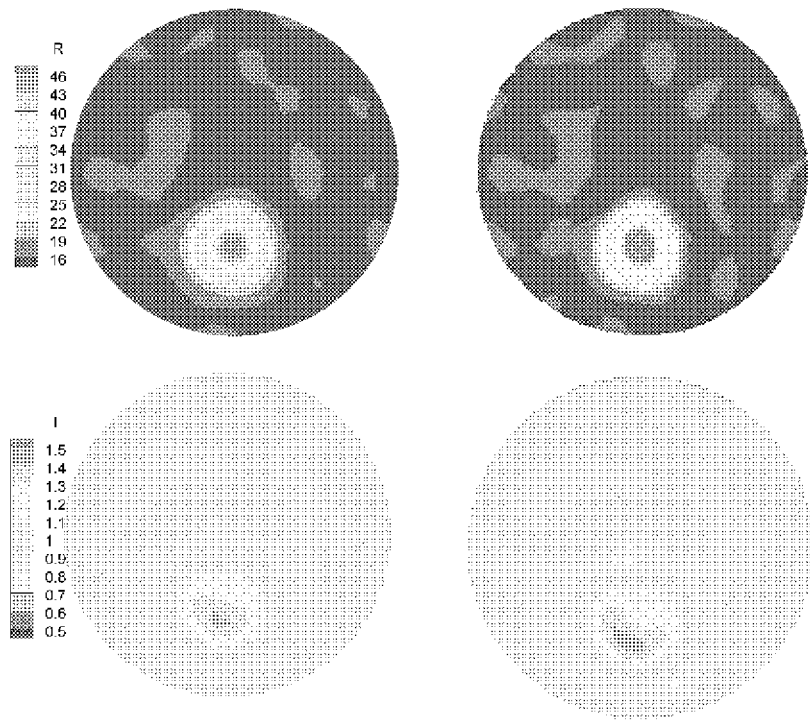
FIG. 5A  FIG. 5B
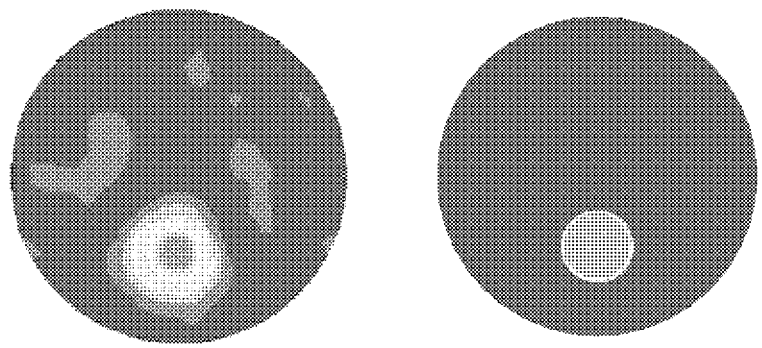
FIG. 5C  FIG. 5D
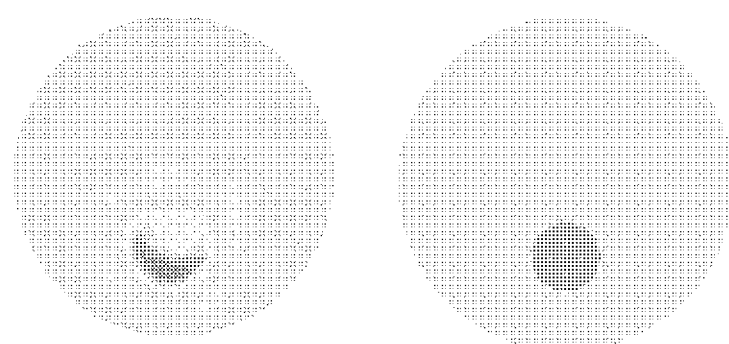

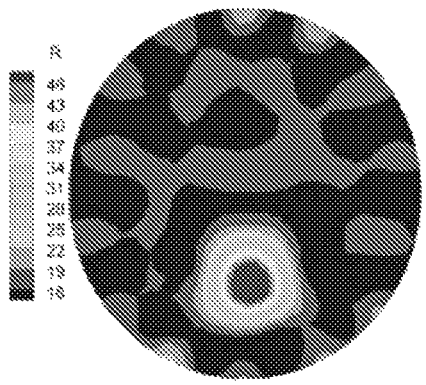 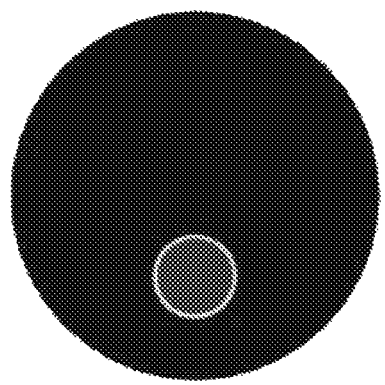
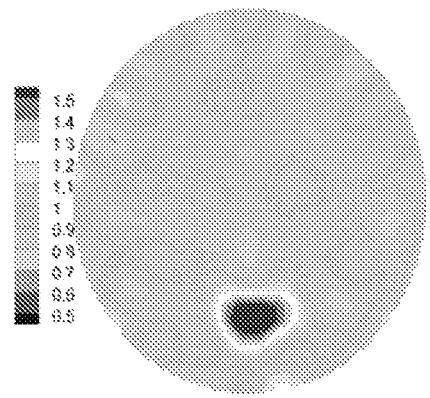 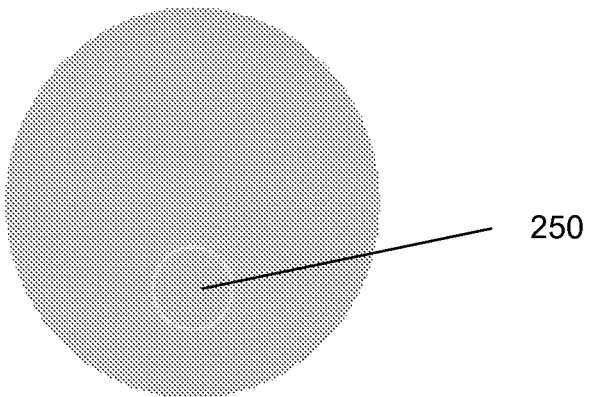
250
FIG. 7A        FIG. 7B

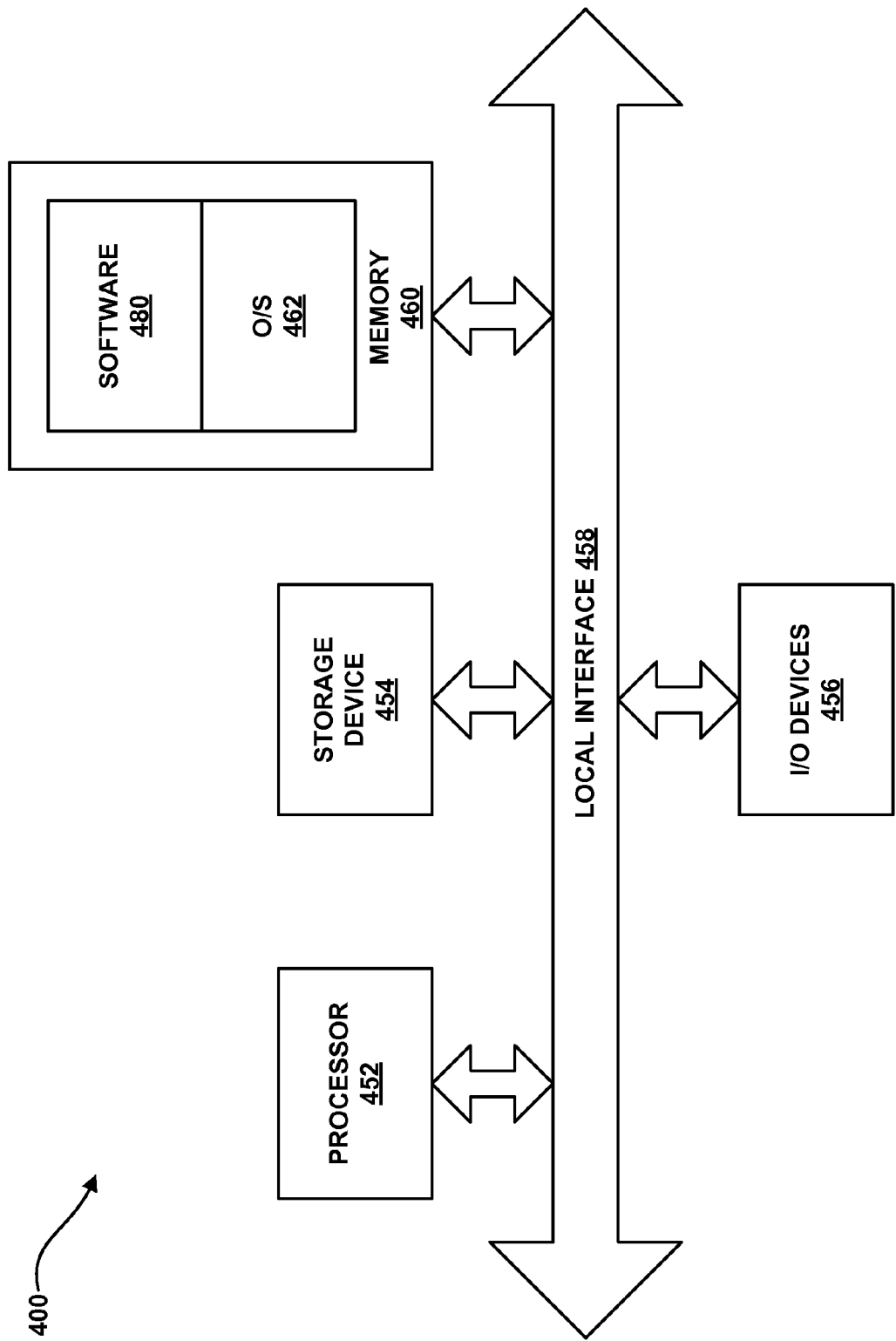

SYSTEM AND METHOD FOR COLLECTION AND USE OF MAGNETIC RESONANCE DATA AND MICROWAVE DATA TO IDENTIFY BOUNDARIES OF INTEREST

CROSS-REFERENCE TO RELATED APPLICATIONS

This application claims the benefit of U.S. Provisional Patent Application Ser. No. 61/302,758 filed Feb. 9, 2010, entitled "SYSTEM AND METHOD FOR COLLECTION AND USE OF MAGNETIC RESONANCE DATA AND MICROWAVE DATA TO IDENTIFY BOUNDARIES OF INTEREST." This provisional application is incorporated herein by reference in its entirety as if fully set forth.

GOVERNMENT SUPPORT

This invention was made with government support under Contract Number P01 CA080139-09 awarded by Alternative Breast Cancer Imaging Modalities (NIH/NCI) and Contract Number R33 CA102938-04 awarded by MR Microwave Absorption and Tomography Imaging (NIH/NCI). The government has certain rights in the invention.

BACKGROUND OF THE INVENTION

Breast cancer is a significant health problem in the United States (US) and accounts for more than 40,000 deaths annually. Early detection is cited as one of the best ways to improve long-term prognosis of a patient. The most common method for detection in clinical practice is X-ray mammography, which is generally effective for the broad population of women over 50 years of age. However, screening mammography has substantial limitations, primarily a high false-positive rate (up to 29%), which can result in unnecessary and costly surgical interventions. Breast cancer detection is a particularly challenging problem in younger women and those with radiographically dense breasts. In these cases, the increased levels of fibroglandular tissue can easily obscure small tumors or masquerade as an abnormality because of the tissue overlap on plain film, and as a result, the overall diagnostic performance of mammography can be significantly degraded.

Mammography has other drawbacks from the perspective of the patient, including uncomfortable and painful breast compression and exposure to ionizing radiation. Other clinical standards, such as ultrasound and magnetic resonance imaging (MRI), have also been used to detect breast cancer. As is known by those having ordinary skill in the art, an MR image is typically a high-resolution grey-scale image; however, the MR image lacks in its ability to provide information about the physiological state of the tissue being imaged, of which physical properties such as permittivity and conductivity could be surrogates for that information. While both ultrasound and MRI can achieve high spatial resolution, neither can provide information about the molecular-level changes occurring in breast tissue at the present time.

Microwave imaging spectroscopy (MIS) is based on recovering the electrical properties, namely, permittivity and conductivity, of tissue. Early studies showed a significant dielectric property contrast between normal and malignant breast tissues, however, more recent data indicates that the properties of the normal breast are more variable than originally thought and that the contrast may not be as great for some types of breast tissue. This is particularly true for radiographically denser breasts with higher concentrations of fibroglandular tissue. Notwithstanding, early clinical microwave imaging studies on patients with suspected tumors has demonstrated significant discrimination between those with malignant cancers versus those with benign lesions and other normal tissues. In addition, the non-ionizing and non-compressive nature of microwave imaging makes the technique potentially attractive for cancer screening.

MIS mainly includes solving two problems: a forward problem and an inverse, or optimization, problem. The forward problem involves computing the output from known inputs, namely, microwave excitation, and system properties, such as dielectric property distribution of the tissue being imaged, whereas the inverse problem estimates the properties of an unknown volume, namely dielectric properties of the tissue, from known input, namely, microwave excitation, and measured field values. Since the inverse electromagnetic problem is non-linear, the image reconstruction process is solved iteratively. Moreover, because of its non-linear and ill-posed nature, Gauss-Newton schemes are well suited to the application but require some form of regularization to impose additional constraints.

Regularization is often accomplished by introducing a priori information about the tissue being imaged, which can be necessary to ensure convergence of the reconstruction algorithm to the correct electromagnetic property distribution. In the field of microwave imaging, a number of studies have investigated the incorporation of different types of priors ranging from the internal and/or external shape of the body to information about tissue dielectric properties including their upper and lower bounds.

Given the advantages and limitations of microwave imaging, it would be beneficial to combine the functional information of the microwave imaging with high spatial resolution of other imaging techniques such as, for example, MR.

SUMMARY OF THE INVENTION

Embodiments of the present invention provide a system and method for collection and use of magnetic resonance data and microwave data to identify boundaries of interest. Briefly described, a first aspect of the present invention is directed to a method for use of spatial resolution data and microwave data to identify region boundaries of interest in soft tissue. The method includes the steps of simultaneously gathering spatial resolution data and microwave data from the soft tissue, creating a customized mesh segmented into multiple subzones from spatial information resulting from the gathered spatial resolution data, and performing image reconstruction using spatial information resulting from the gathered spatial resolution data and gathered microwave data.

A second aspect of the present invention is directed to a method for use of spatial resolution data and microwave data to identify region boundaries of interest in a rigid structure. The method includes the steps of gathering spatial resolution data from the rigid structure, gathering microwave data from the rigid structure, creating a customized mesh segmented into multiple subzones from spatial information resulting from the gathered spatial resolution data, and performing image reconstruction using spatial information resulting from the gathered spatial resolution data and the gathered microwave data.

Briefly describe, in architecture, a third aspect of the present invention is directed to a system for use of spatial resolution data from a subject and microwave data from the subject to identify region boundaries of interest in tissue diagnosis. The system includes a microwave imaging array comprising a plurality of antennas located substantially in a circle. Each of the plurality of antennas configured to sequentially transmit a signal in turn, while each of the non-transmitting antennas act as receivers. The system also includes a spatial resolution imaging scanner and a processor configured to process data from the microwave imaging array and the spatial resolution imaging scanner.

In a system for use of spatial resolution data and microwave data to identify boundaries of interest in tissue, a fourth aspect of the present invention is directed to a machine readable medium. The machine readable medium includes instructions to perform the steps of gathering spatial resolution data and microwave data from the tissue, creating a customized mesh segmented into multiple subzones from spatial information resulting from the gathered spatial resolution data, and performing image reconstruction using spatial information resulting from the gathered spatial resolution data and gathered microwave data.

Other systems, methods and features of the present invention will be or become apparent to one having ordinary skill in the art upon the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principals of the invention.

FIGS. 5A-5D show reconstructed permittivity and conductivity images.

FIGS. 7A and 7B provide 1300 MHz reconstructed permittivity and conductivity images of the phantom experiment contrasting the original Tikhonov algorithm and the present soft prior approach.

FIG. 11A illustrates permittivity and FIG. 11B illustrates conductivity.

FIG. 15 is a schematic diagram of the first exemplary embodiment of a general-purpose computer architecture that can implement the present imaging system.

DETAILED DESCRIPTION

The present invention combines the functional information available through microwave imaging, namely, property contrast, with the high spatial resolution of MR or X-ray CT by implementing a soft prior regularization. In this way, the present system and method enhances quality of previous results by recovering more accurate dielectric property distributions and ultimately, detects even smaller tumors. It should be noted that for exemplary purposes, the following description refers to the use of MR imaging, although other modalities are capable of providing the spatial information gathered from MR imaging.

Use of the present system and method improves both the sensitivity and specificity of current microwave imaging techniques, and also supplies more functional information about tissue health. These properties can include electrical or optical characteristics, temperature, or tissue.

The present system and method may be separated into two main embodiments, specifically, a first embodiment for imaging and reconstruction of soft tissue, and a second embodiment for imaging and reconstruction of rigid structures. The following describes these embodiments in detail. It should also be noted that the present invention may provide imaging and reconstruction in two dimensions or three dimensions. Both, two-dimensional and three-dimensional imaging and reconstruction, are described in detail herein.

Figure 1:
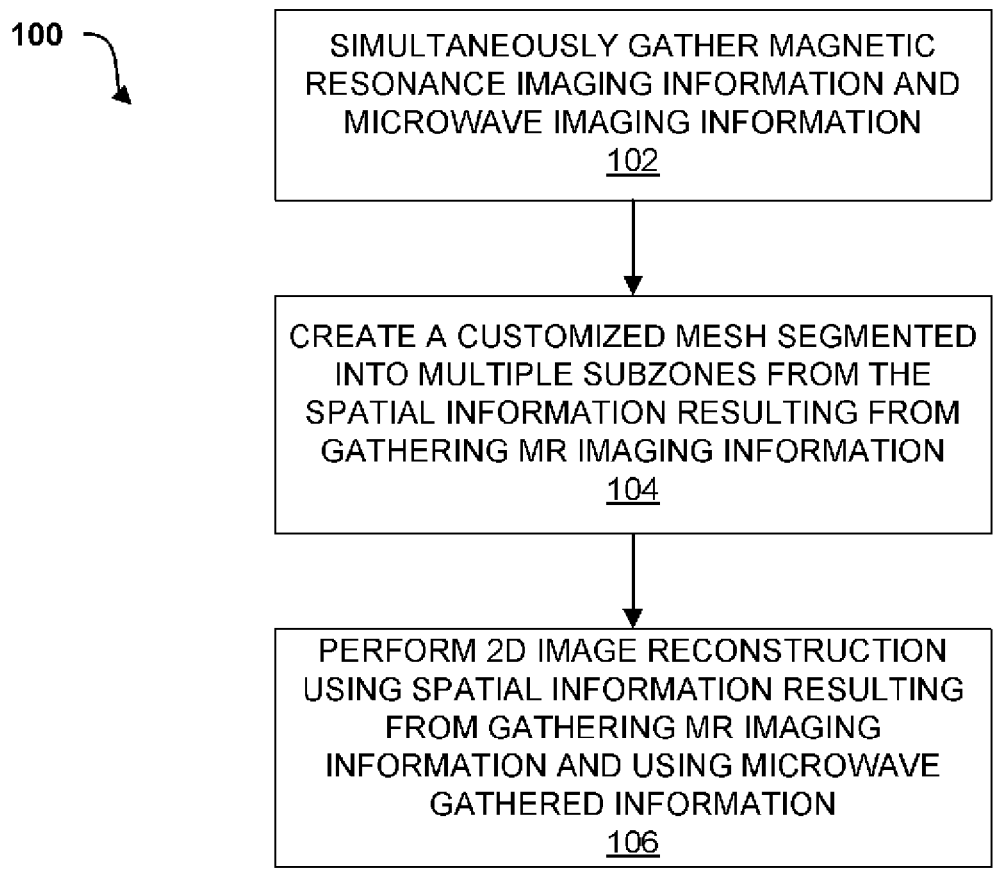
FIG. 1 is a flowchart illustrating steps taken in collecting and using magnetic resonance data and microwave data to identify boundaries of interest in soft tissue.

FIG. 1 is a flowchart 100 illustrating steps taken in collecting and using magnetic resonance data and microwave data to identify boundaries of interest in soft tissue. It should be noted that FIG. 1 demonstrates the case where imaging is provided in two dimensions. Any process descriptions or blocks in flowcharts should be understood as representing modules, segments, or portions of code which include one or more executable instructions for implementing specific logical functions or steps in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

As shown by block 102, Magnetic Resonance (MR) and microwave data is simultaneously gathered from soft tissue being tested. An example of soft tissue may be, for example, a breast. It should be noted that MR imaging information and microwave imaging information are gathered simultaneously for soft tissue due to soft tissue being deformable. Gathering MR and microwave simultaneously may provide substantially exact spatial registration between the MR imaging information and the microwave imaging information. Since MR imaging is performed in air, while microwave imaging is typically performed in a liquid, and because certain tissue types such as the breast are buoyant in the liquid, it is difficult to have soft tissue positioned in the exact same manner during each separate imaging process. As a result, if MR imaging information were gathered separate from microwave imaging information, soft tissue may not have the same shape, thereby resulting in it not being possible to combine MR imaging information with microwave imaging information for an accurately correlated and combined image.

The MR imaging information gathered includes spatial information of the tissue under test resulting in analysis of a single plane of the soft tissue under examination. Each planar MR image can be segmented into different regions depending on the appearance of the image. Continuous dark regions can be grouped into one area while continuous lighter zones are segmented into another. This segmentation essentially embodies the spatial information of the MR image.

Figure 2A:
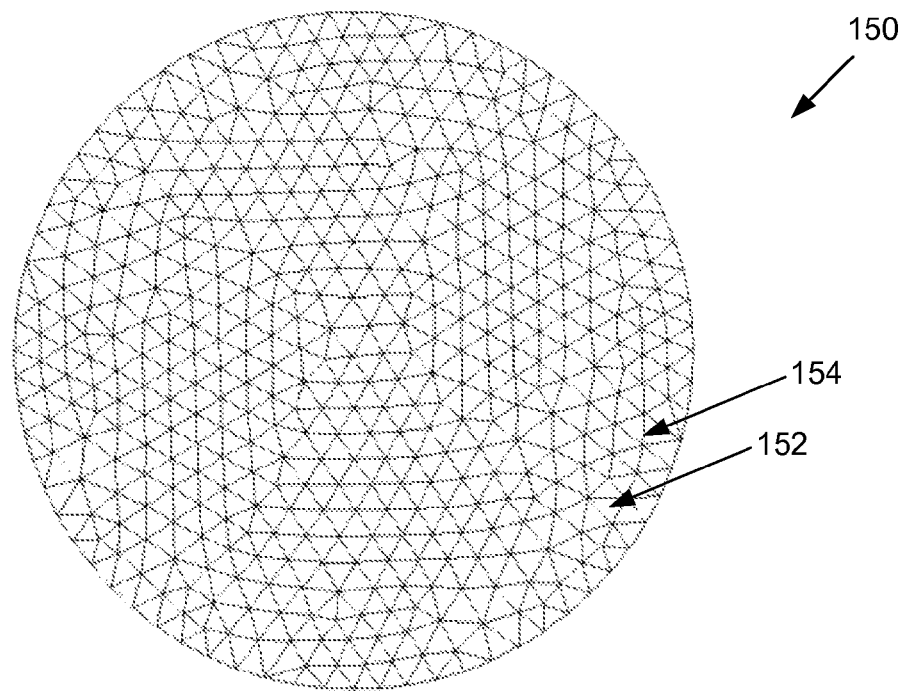
FIGS. 2A and 2B are schematic diagrams illustrating examples of a customized triangular mesh.
Figure 2B:
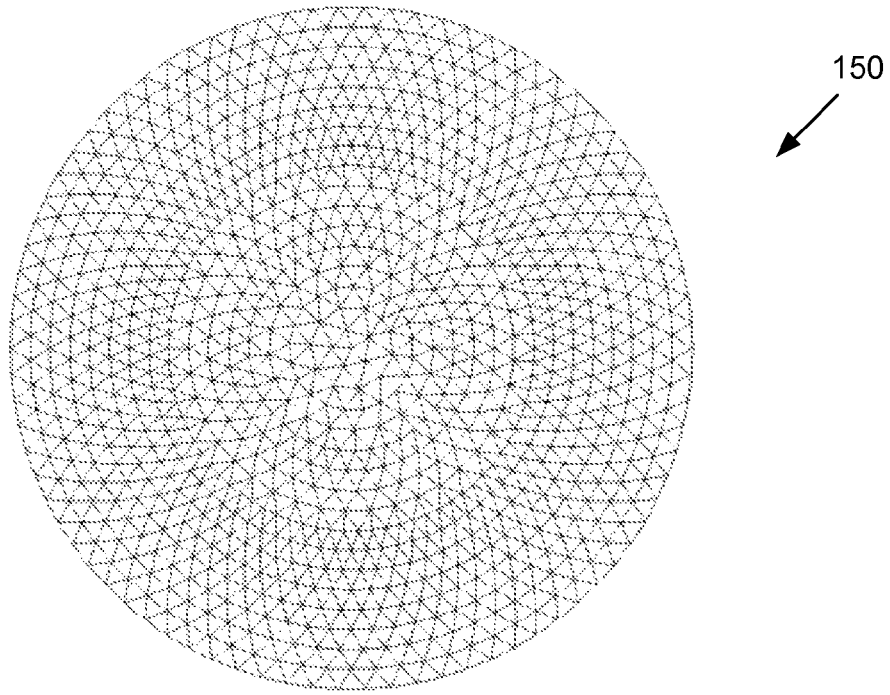

As shown by block 104, the spatial information resulting from gathering MR data is used by a computer (FIG. 15) to create a customized mesh. As shown by FIG. 2, which is a schematic diagram illustrating an example of a customized triangular mesh 150, nodes 152 of the mesh 150 are connected by connecting lines 154. For the exemplary embodiment of FIG. 2, triangular spaces between the nodes 152, are referred to herein as elements. It should be noted that the spaces may instead be shaped in a different manner, such as, for example, as quadrilaterals. The MR imaging information does not provide electrical properties of the soft tissue. It is noted that FIG. 2A illustrates a uniform reconstruction mesh with 473 nodes and 872 triangular-elements, while FIG. 2B illustrates a uniform reconstruction mesh with 961 nodes and 1838 triangular elements.

The ultimate functional information resulting from microwave imaging is reflected in the dielectric properties (permittivity and conductivity) of the tissue under examination. Based on previous studies, there is often a strong correlation between tissue physiological state and its dielectric properties. For example, in the breast the permittivity and conductivity of a malignant tissue are higher than those of normal tissue.

An example of processes that may be performed to gather microwave data is described in U.S. Pat. No. 6,448,788, which is entitled, "Fixed array microwave imaging apparatus and method", and U.S. Pat. No. 5,841,288, which is entitled, "Two-dimensional microwave imaging apparatus and methods," each of which is hereby incorporated by reference in its entirety.

Once the MR images corresponding to microwave data is obtained, different regions of the tissue can be segmented and identified on the MR images by using various commercial image processing software. The high spatial resolution of MRI is the key to this process. Based on the location and size of different regions, customized meshes (with nodes at the boundary of each region) can be created.

Returning to FIG. 1, as shown by block 106, customized meshes (with nodes at the boundary of each region) can be incorporated into the microwave image reconstruction process, which is further described for the two-dimensional (2D) case as follows. Specifically, two-dimensional image reconstruction is performed using spatial information resulting from gathering MR imaging information and using microwave gathered information, as described below.

Reconstruction algorithms in microwave imaging are based on determining the distribution of the constitutive parameters within tissue where the dielectric properties are embedded in the squared complex-valued wave number which can be written as shown by equation 1 below.

$$k^2(r) = \omega^2 \mu_0 \epsilon(r) - j\omega\mu_0 \sigma(r) \quad \text{(Eq. 1)}$$

In equation 1, r is the position vector in the imaging domain, ω is the angular frequency, j is the imaginary unit, $\mu_0$ is the free-space permeability, $\in$ is the permittivity, and σ is the conductivity.

Calculation of the forward solution is based on the 2-D form of Maxwell's equations and is computed using a finite difference time domain (FDTD) algorithm, whereas the reconstruction process is based on a Gauss-Newton iterative approach with a variance stabilizing transformation in which the measured electric field vector $E^m$ is matched iteratively with the computed electric field vector $E^c(k^2)$ calculated using the forward model for a given distribution of the constitutive parameters stored in the vector $k^2$. In the 2D FDTD method, a frequency domain forward field response is produced for each transmitter and the individual field values are extracted at each receiver location. The length of the vector $k^2$ is N, the number of reconstruction parameters.

In order to overcome the ill-posedness of the problem, constraints on the reconstructed image are required. In the present algorithm, Tikhonov regularization is used to stabilize the reconstruction procedure, albeit with added smoothing. The objective function is illustrated by equation 2 below.

$$\Omega = \|\Gamma^m - \Gamma^c(k^2)\|_2^2 + \|\Phi^m - \Phi^c(k^2)\|_2^2 + \lambda \|L(k^2 - k_0^2)\|_2^2 \quad \text{(Eq. 2)}$$

In equation 2, $\Gamma^m$ and $\Gamma^c$ are the log magnitudes and $\Phi^m$ and $\Phi^c$ are the phases of the measured and computed field values, respectively, λ is the weighting coefficient, also known as the Tikhonov regularization parameter, and L is a positive definite, dimensionless regularization matrix.

$k_0^2$ is a prior estimate of $k^2$ and $\|.\|_2$ is the two-norm of a vector. In this case O is the number of measurements. The two-norm of a vector is the square root of the sum of the squares of the complex modulus of its elements shown in equation 3 below.

$$\|v\|_2 = \sqrt{\sum_{i=1}^{l} |v_i|^2} \quad \text{(Eq. 3)}$$

Equation 2 can be solved for the iterative property update, $\Delta k_\eta^2$ resulting in equation 4 below.

$$[J^T J + \lambda L^T L]\Delta k_\eta^2 = J^T \begin{bmatrix} \Gamma^m - \Gamma^c(k_\eta^2) \\ \Phi^m - \Phi^c(k_\eta^2) \end{bmatrix} - L^T L(k_\eta^2 - k_0^2) \quad \text{(Eq. 4)}$$

In equation 4, J is the Jacobian matrix, which has dimensions 2O×2N and contains derivatives of the log magnitude and phases of the computed field values with respect to the property values at each of the N reconstruction parameter mesh nodes. $k_\eta^2$ is the vector $k^2$ at iteration η and is updated as shown by equation 5 below.

$$\Delta k_\eta^2 = k_{\eta+1}^2 - k_\eta^2 \quad \text{(Eq. 5)}$$

This implementation is referred as a Gauss-Newton iterative algorithm with a variance stabilizing transformation. In addition, a dual-mesh approach is used where the forward solution is computed on a rectangular uniform FDTD lattice, while the electromagnetic property parameters are reconstructed on a triangular element mesh, which is placed concentrically within an antenna array. For exemplary purposes, the antenna array may have a diameter d=14 cm, and contain 473 nodes and 872 triangular elements, as shown by FIG. 2A. To allow the study of the effect of number of nodes on the reconstructed images, another triangular element mesh having 961 nodes, as shown by FIG. 2B, may be used instead.

In the reconstruction algorithm prior to the present invention, no prior spatial information was used, and the regularization matrix L in equation 4 was set to the identity matrix, which applies the same weight to the values at all nodes within the imaging domain. In addition, for the right hand term in equation 4, $k_0^2$ was set to $k_\eta^2$ as is the case for Levenberg-Marquardt algorithms, leading to a simplified version of the update equation, as shown by equation 6 below.

$$[J^T J + \lambda I]\Delta k_\eta^2 = J^T \begin{bmatrix} \Gamma^m - \Gamma^c(k_\eta^2) \\ \Phi^m - \Phi^c(k_\eta^2) \end{bmatrix} \quad \text{(Eq. 6)}$$

In the present invention, this reconstruction algorithm with no prior spatial information about the structure of the tissue (or phantom) being imaged is referred as the original Tikhonov algorithm. For exemplary purposes, the uniform triangular element mesh containing 473 nodes and 872 triangular elements, as shown by FIG. 2A, was used for reconstruction with no spatial prior information. To allow the study of effect of number of nodes on the reconstructed images, another triangular element mesh may instead have 961 nodes and 1838 triangular elements, as shown by FIG. 2B.

The reconstruction algorithm of the present system and method includes prior spatial information about the shape of the boundary of each region within the tissue (or phantom) being imaged. This method is called "soft prior regularization" and the basic idea behind it is to penalize the variation within regions that are assumed to have the same or similar dielectric properties. As already described, these regions are determined based on corresponding high spatial resolution sources, such as MR images. In the soft prior regularization algorithm, when two different regions share the same boundary, the smoothing across their common interface is restricted. The a priori information about the structure of the imaged tissue is incorporated into the soft prior regularization algorithm through the regularization matrix, L in equation 4. According to known information about the structure of the tissue, derived from any high spatial resolution source, such as MR images, each node in the reconstruction mesh is labeled with an associated region number.

Given two nodes, i and j, in the reconstruction mesh, with their associated matching regions, $R_i$ and $R_j$, the corresponding entry in the L matrix is defined as shown by equation 7 below. It should be noted that equation 7 is also referred to herein as the regularization matrix.

$$L_{ij} = \begin{cases} 0 & \text{if } R_i \neq R_j \\ \frac{-1}{N} & \text{if } R_i = R_j \\ 1 & \text{if } i = j \end{cases} \quad \text{(Eq. 7)}$$

In equation 7, N is the number of nodes in region $R_i$. Based on the construction of L as illustrated above, $L^T L$ in equation 4 is an approximation of a second order Laplacian smoothing operator inside each region, which limits the smoothing across the boundary of distinct regions. Since the structure of the tissue being imaged does not change during the iterative image reconstruction algorithm, both the regularization matrix L and Laplacian smoothing operator $L^T L$, can be calculated once and stored at the beginning of the procedure. In this way, redundant calculations are avoided and the algorithm becomes more efficient.

In practice, the abovementioned is provided to allow a user to determine permittivity and conductivity of the tissue under test at different nodes. As is known by those having ordinary skill in the art, tissue having higher electrical properties than other tissue within tissue under test may represent a tumor or other region of interest that requires further analysis.

Specifically, in practice, each node is defined as being within a specific region, as previously mentioned. The L matrix of equation 7 is then defined, which is inserted into equation 4 to allow for the solving of the squared complex-valued wave number, k, iteratively in equation 2. Once k is solved for, it is placed into equation 1 to allow for obtaining permittivity ($\epsilon$) and conductivity ($\sigma$) at different positions, r, in the imaging domain.

As previously mentioned, for the present system and method, microwave exams (imaging) are performed at the same time as the MR exams (imaging), and therefore, the microwave exams are performed in an MR bore simultaneously with the MR image acquisition. Therefore, accurate segmentation of the MR-based anatomical structures into microwave reconstruction meshes is possible. The present soft prior regularization approach has been applied to several simulation and phantom experiments with known structural shape, size, and location. The following provides an example of a system that may be used for breast imaging and data acquisition. It should be noted that the present invention is not limited by the present exemplary breast imaging system description.

Figure 3:
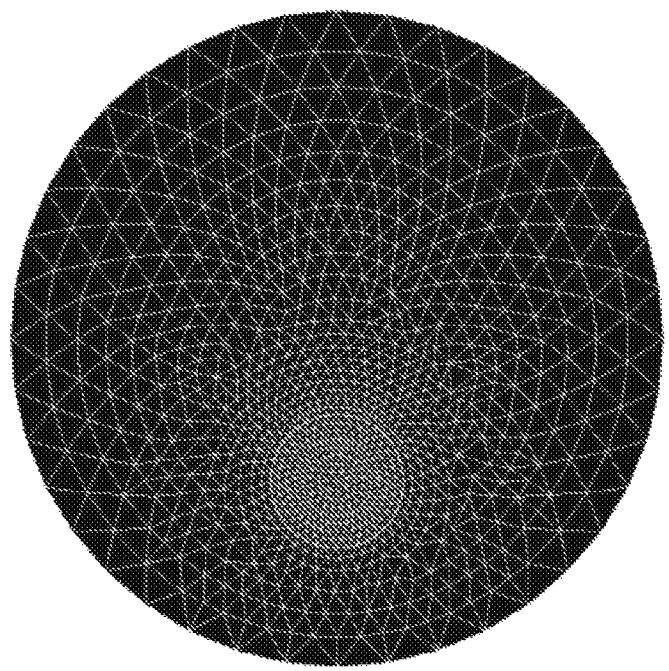
FIG. 3 shows a customized reconstruction mesh used for simulation and phantom experiments.

FIG. 3 shows the customized reconstruction mesh used for simulation and phantom experiments presented here. This mesh contains 915 nodes and 1708 triangular elements and is created based on the schematic configuration of the experiments illustrated in FIG. 4. The target inclusion was a 1.4 cm radius thin-wall plastic cylinder centered at 3 cm below the imaging zone center and filled with a mixture of 55:45 glycerin:water. The inclusion was surrounded by a coupling bath comprised of an 86:14 glycerin:water mixture that is sufficiently lossy to fully dampen unwanted reflections from the tank walls and base. The imaging array 200 contains 16 monopole antennas 202 located on a 15.2 cm diameter circle. Operating frequency used ranged from 500 MHz to 2.5 GHz and each antenna channel operated in both transmit and receive modes. At any given time, each antenna transmits a signal, while the other 15 act as receivers. This process is sequentially repeated for all antennas and as a result, 240 (16 transmitter×15 receivers) measurements of the scattered field are obtained and used in the reconstruction process. At 1300 MHz, the actual permittivity and conductivity values of the coupling liquid and the tumor inclusion were $\epsilon_{r,bk}$=15.60, $\sigma_{bk}$=0.90 S/m, $\epsilon_{r,Tu}$=51.16, and $\sigma_{Tu}$=1.44 S/m, respectively.

Error Analysis

Since the true values of the dielectric property distribution are known in simulations and phantom experiments, the relative error between the true property distribution and the estimated values can be computed as shown by equation 8 below.

$$err = \sum_{n=1}^{N} \frac{|V_{(n)}^{recon} - V_{(n)}^{exact}|}{V_{(n)}^{exact}} \quad \text{(Eq. 8)}$$

In equation 8, $V_{(n)}^{recon}$ is the reconstructed dielectric property value (either permittivity or conductivity) at node n (in the reconstruction mesh), whereas $V_{(n)}^{exact}$ is the true value of the selected dielectric property at that location.

Since the nodes in the meshes are not uniformly distributed, a weighting factor has been applied to each location to reduce the bias that is associated with the area of the elements surrounding each node with respect to the total imaging area, which leads to the weighted error definition shown by equation 9 below.

$$err_w = \sum_{n=1}^{N} w_n \frac{|V_{(n)}^{recon} - V_{(n)}^{exact}|}{V_{(n)}^{exact}} \quad \text{(Eq. 9)}$$

In equation 9, $$w_n = \frac{A_n}{A},$$

$A_n$ is the area of the elements surrounding node n, and A is the total imaging area. Due to the iterative nature of the reconstruction procedure, a stopping criterion is needed to terminate the algorithm. Since in general the algorithm converges within 15 iterations, all reconstructions are allowed to execute for 20 iterations as a simple way to ensure convergence.

Results

Figure 4:
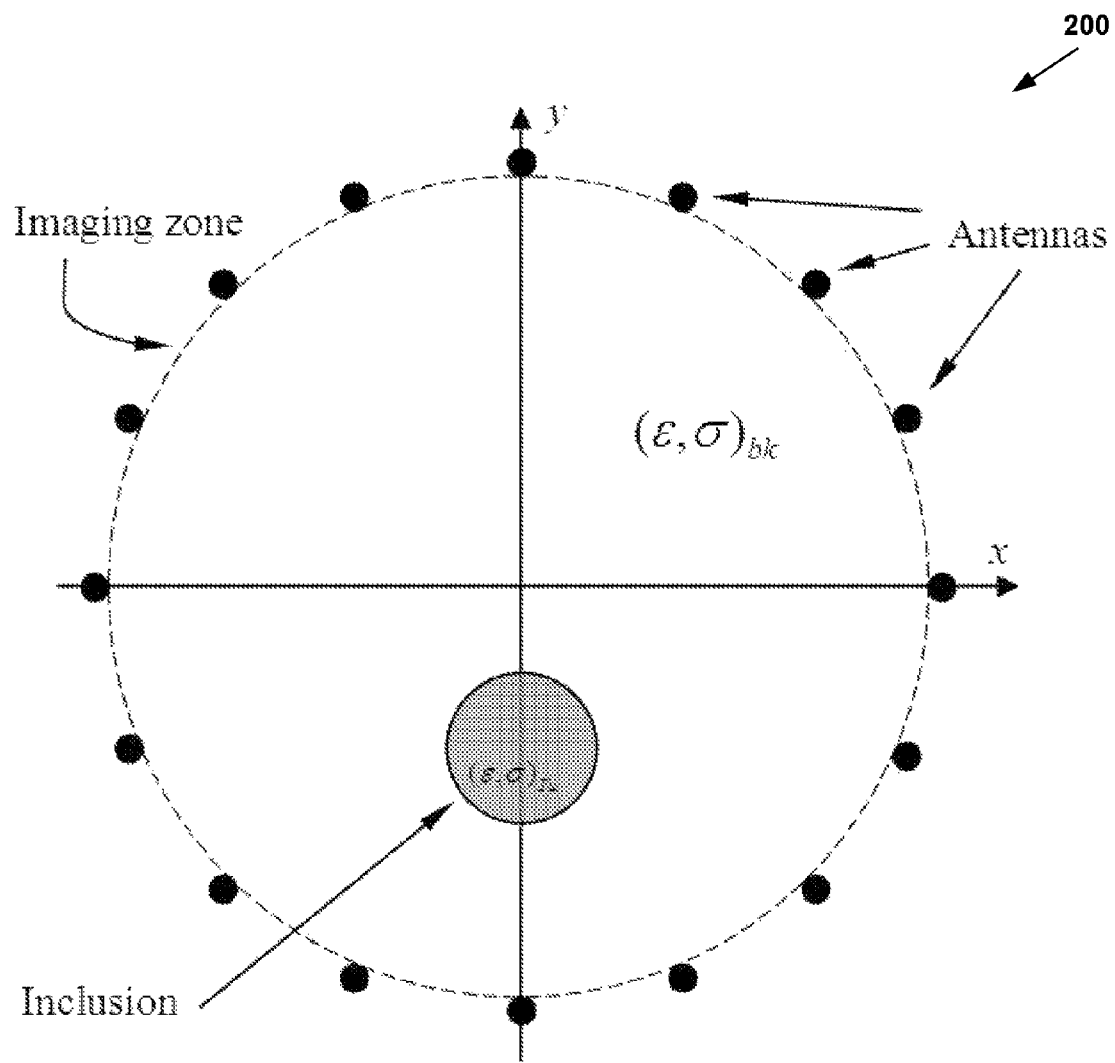
FIG. 4 is a schematic diagram of a microwave antenna array positioned around an imaging zone.
Figure 6A:
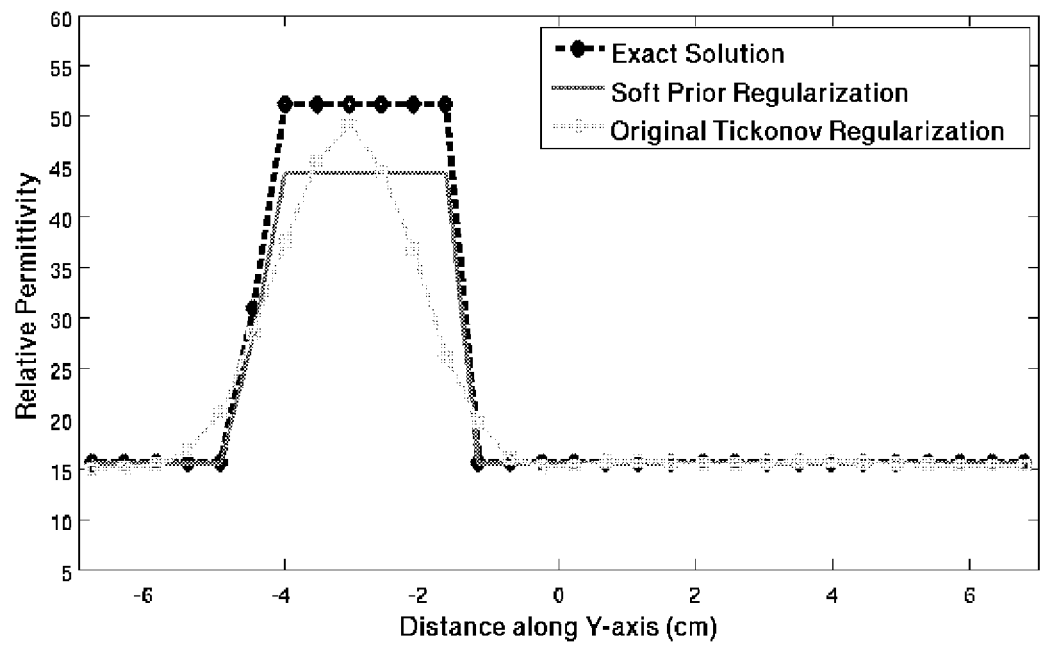
FIGS. 6A-6D are graphs comparing reconstructed and true dielectric properties collected under the first embodiment.
Figure 6A:
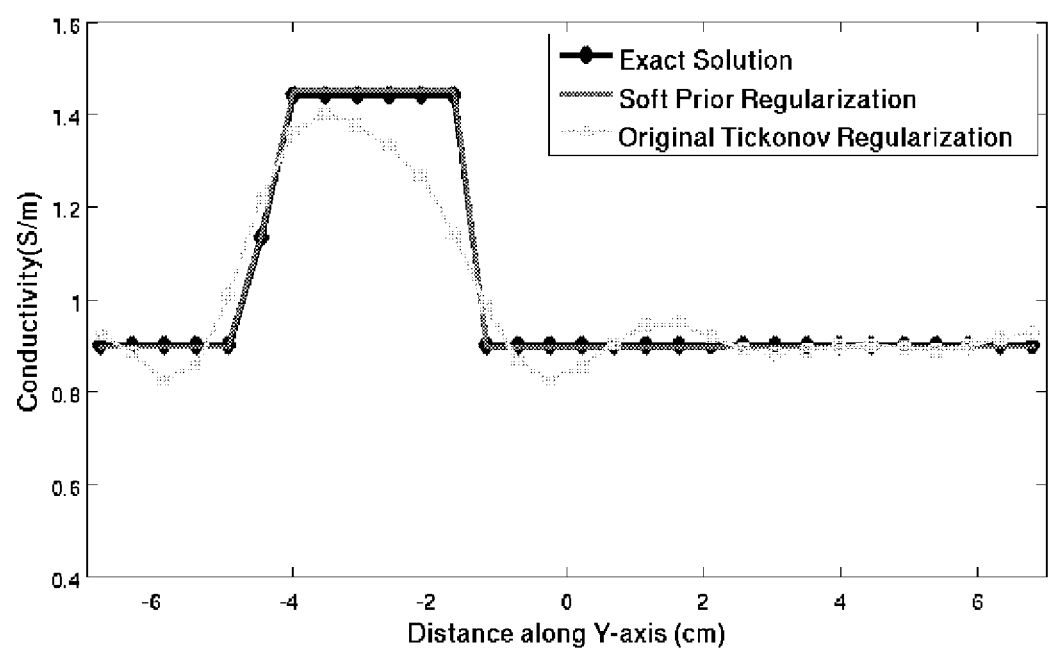
Figure 6B:
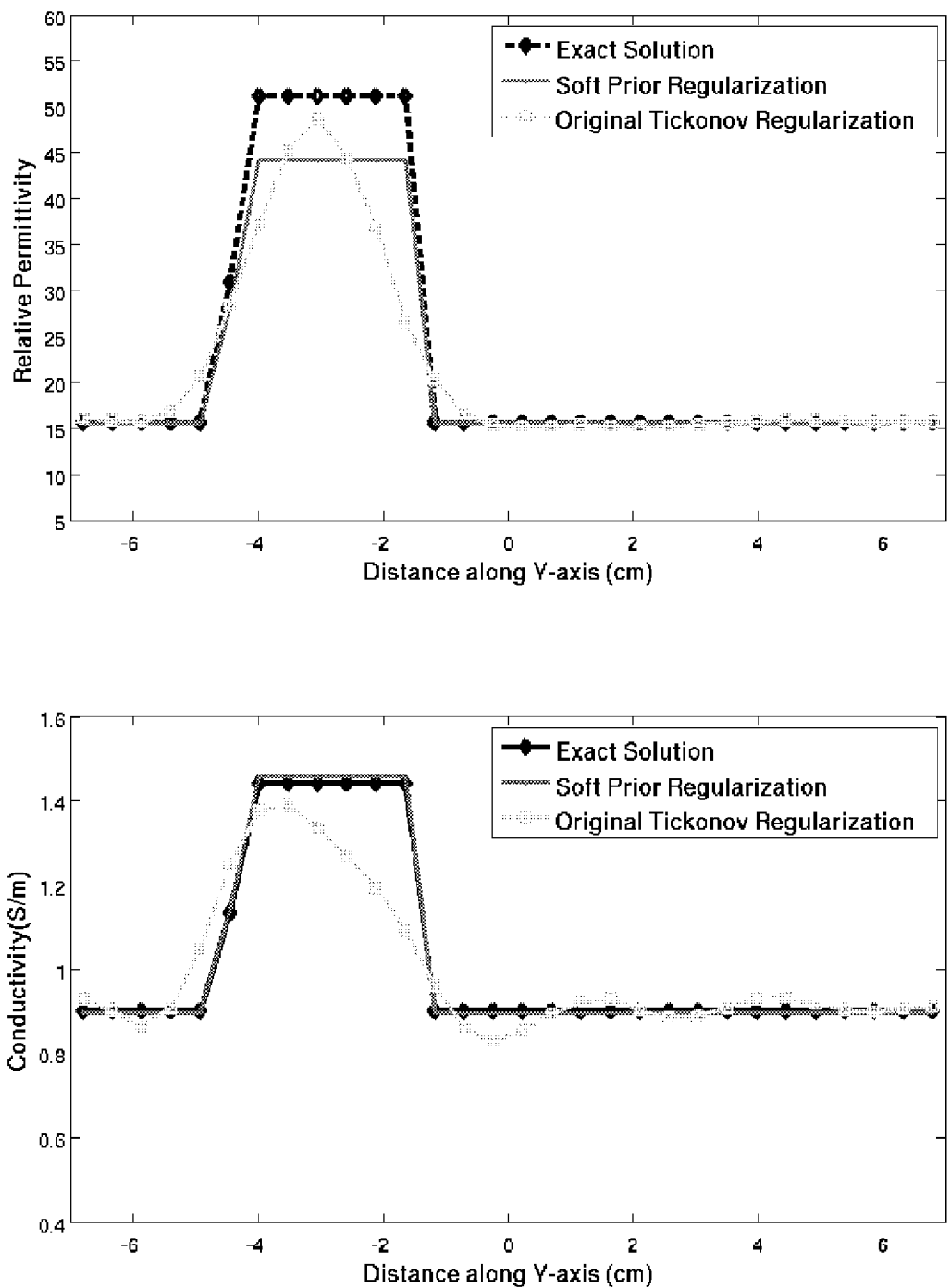
Figure 6C:
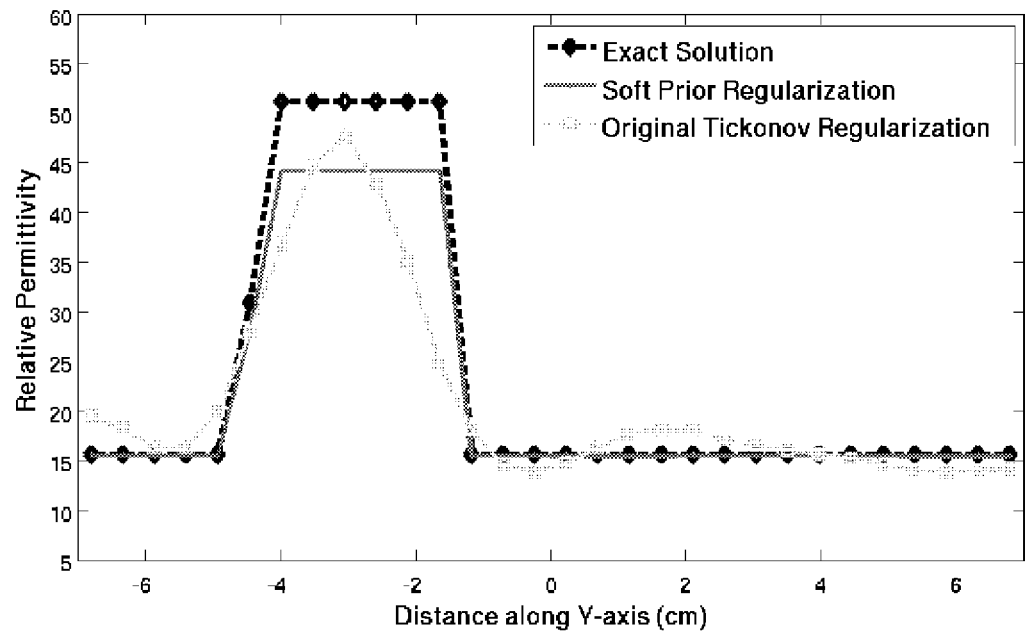
Figure 6C:
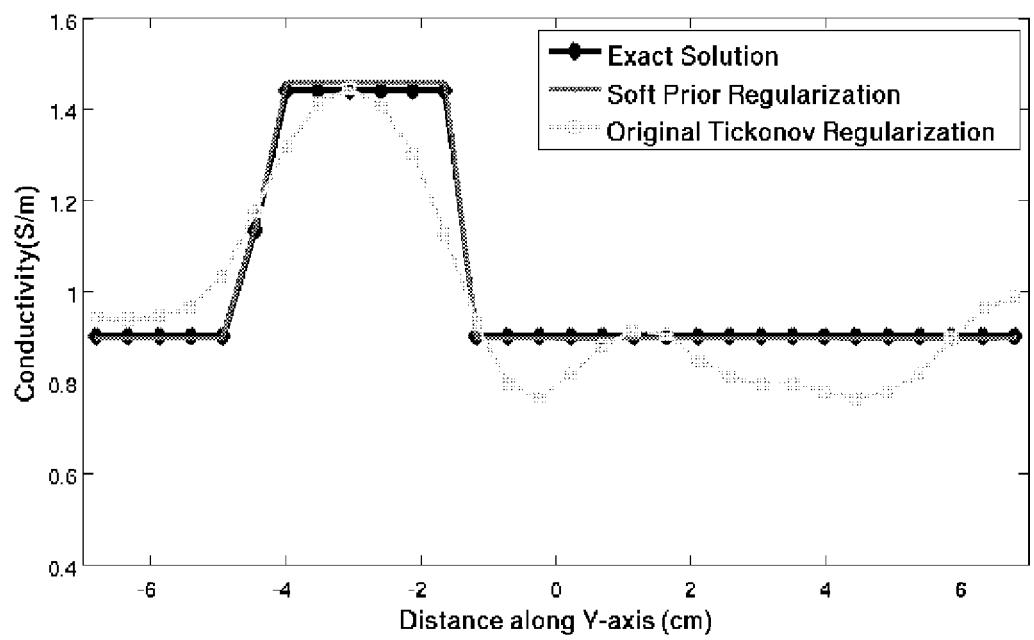
Figure 6D:
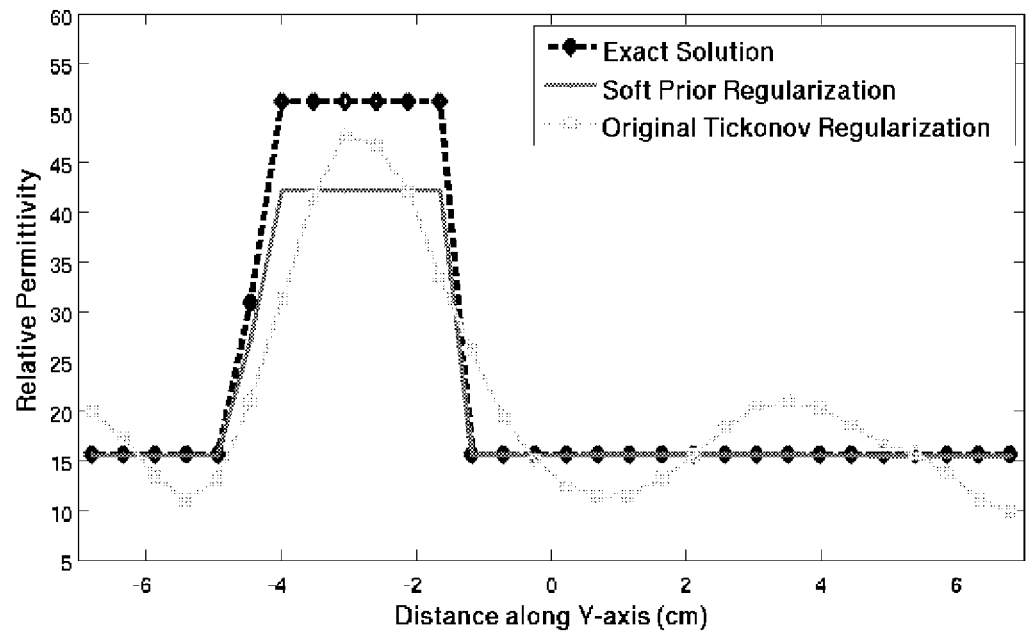
Figure 6D:
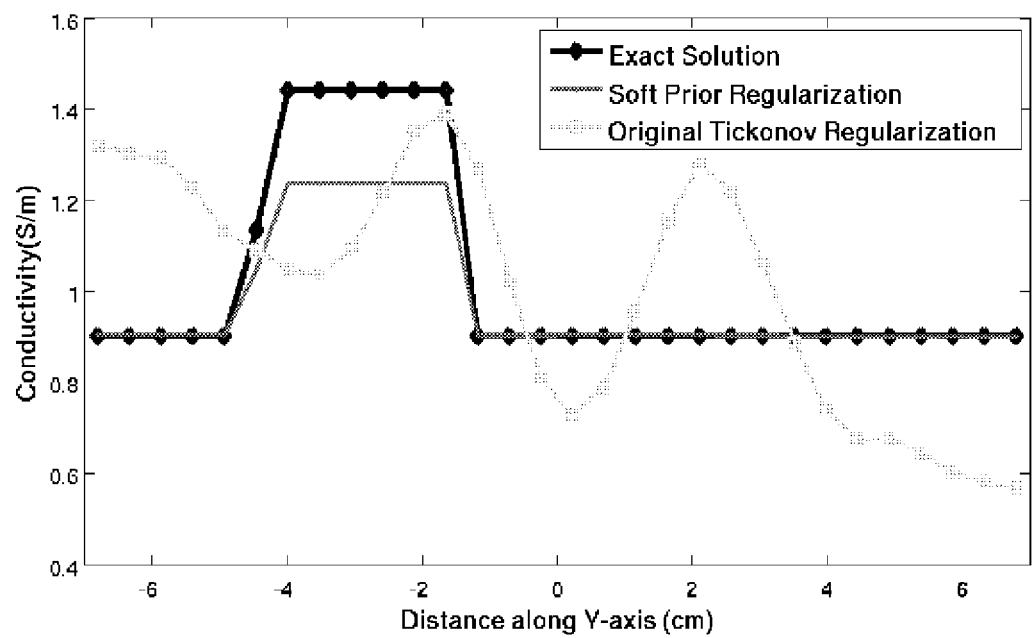

Simulated 2D measurement data was generated by a hybrid boundary element/finite element approach for the single target shape in FIG. 4. An example of a hybrid boundary element/finite element approach is described in U.S. Pat. No. 5,841,288, which is entitled, "Two-dimensional microwave imaging apparatus and methods," which has been incorporated by reference herein in its entirety. The images were reconstructed at 1300 MHz using the Tikhonov algorithm of equation 6 with no spatial information (on 473, 961, and 915 node meshes in FIG. 2 and FIG. 3), and the soft prior regularization approach (on the 915 node mesh in FIG. 3) of equations 4 and 7.

A cylindrical inclusion centered at (x,y)=(0, −3 cm), with a radius of 1.4 cm and dielectric properties of $\epsilon_{r,Tu}$=51.16 and $\sigma_{Tu}$=1.44 S/m was embedded in a background medium with dielectric properties of $\epsilon_{r,bk}$=15.60 and $\sigma_{bk}$=0.90 S/m. Noise ranging from −110 dBm to −80 dBm was added to the simulated measurement data. FIGS. 5A-5D show the 1300 MHz reconstructed images (noise level of −100 dBm) using the original Tikhonov (on the 473, 961, and 915 node meshes) and the new soft prior regularization approaches (on the 915 node mesh), respectively. Specifically, the top images of FIG. 5 are reconstructed permittivity images, while the bottom images are reconstructed conductivity images. Describing FIG. 5 in detail: the images of FIG. 5A are for the prior Tikhonov algorithm of equation 6 with 473 node mesh; the images of FIG. 5B are for the prior Tikhonov algorithm of equation 6 with 961 node mesh; the images of FIG. 5C are for the prior Tikhonov algorithm of equation 6 with 915 node mesh with preferential node deployment in the inclusion; and, the images of FIG. 5D are for the present soft prior approach of equations 4 and 7, with 915 node mesh.

It should be noted that results from the present soft prior technique of equations 4 and 7 are more accurate in terms of location of the inclusion and recovered property values. In addition, recovered background permittivity and conductivity values are much more uniform for the present soft prior case than for the original Tikhonov algorithm technique. Comparing FIGS. 5A, 5B, 5C, and 5D confirms that these improvements are not due to the reconstruction mesh, but due to the regularization matrix of equation 7. The weighted permittivity and conductivity errors (according to equations 8 and 9) for the original Tikhonov approach of equation 6 were 0.172 and 0.128, respectively, while those for the present soft prior approach of equations 4 and 7 were reduced approximately by a factor of 10 to 0.028 and 0.016, respectively. Of course, this is again just in accordance with the present example.

In order to compare the reconstructed and the true dielectric properties in the simulation, vertical transects for the permittivity and conductivity images along a y-axis are shown in FIG. 6, comparing the original Tikhonov algorithm approach to the present soft prior approach, with added noise levels of −110 dBm (FIG. 6A), −100 dBm (FIG. 6B), −90 dBm (FIG. 6C), and −80 dBm (FIG. 6D), respectively. In each figure, the plot on the top corresponds to the permittivity, while the plot on the bottom corresponds to conductivity.

As illustrated in FIG. 6, artifacts increased in both the permittivity and conductivity images from the original Tikhonov algorithm as the noise level rose, especially for the −80 dBm conductivity images where the fluctuations are significant. However, the soft prior regularization approach of the present invention tolerates the added noise much better with relatively minor decreases in the recovered inclusion permittivity and only slightly greater reductions in conductivity. Using the present regularization method, in the present simulation example, the reconstructed permittivity values at all noise levels were underestimated (~10-15%) in the inclusion region. Notwithstanding, the present method clearly detected the inclusion given the large property contrast with the background. In addition, even when considerable noise was added to the measured data (−90 dBm), the present soft prior algorithm recovered the inclusion conductivity values very accurately, and started to underestimate (~15%) its property values at even higher noise levels (−80 dBm).

In order to illustrate other aspects of the present soft prior algorithm, several phantom experiments were performed at 1100 MHz, 1300 MHz, 1500 MHz, and 1700 MHz. The schematic configuration for this study was similar to that of the simulation test described above. A 1.4 cm radius, thin-walled plastic cylinder filled with a mixture of 55% glycerin and 45% water was offset vertically in the background medium (86:14 glycerin:water mixture). The 2D horizontal cross-section of the setup was identical to the schematic shown in FIG. 4.

The following further compares results from use of the original Tikhonov regularization of equation 6 to results from use of the present soft prior approach of equations 4 and 7.

Figure 8A:
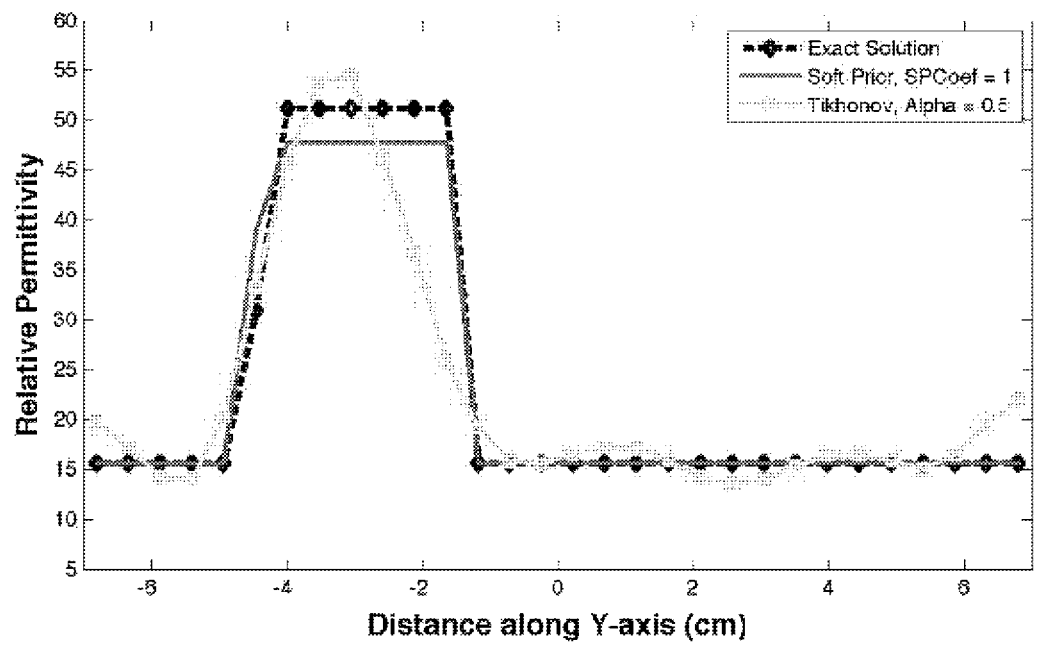
FIGS. 8A-8B are graphs comparing reconstructed and true dielectric properties collected using modified parameters.
Figure 8B:
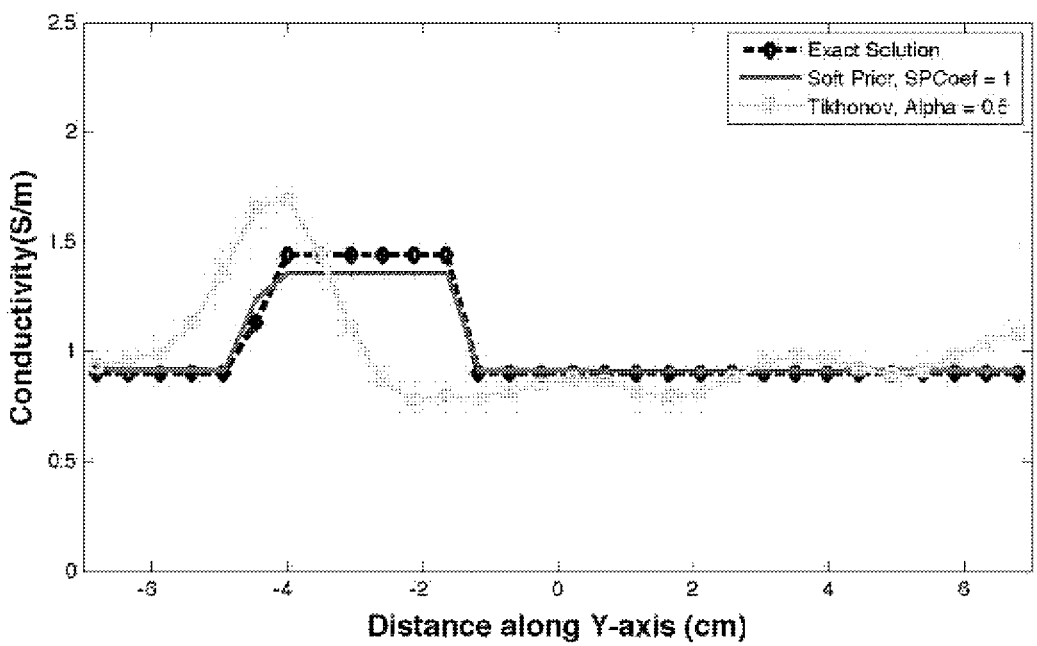
Figure 9A:
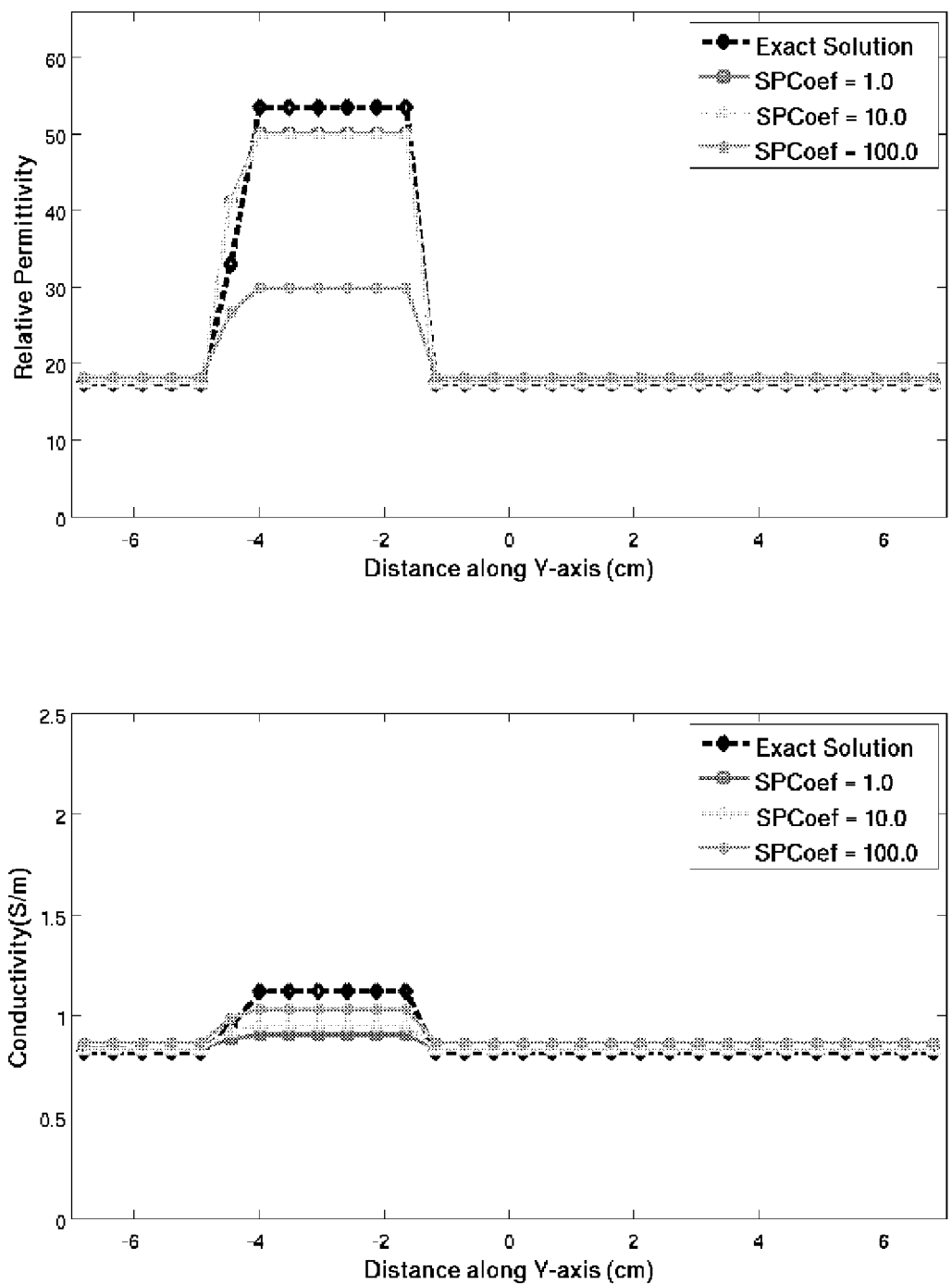
FIGS. 9A-9D are graphs of transects along the y-axis of the reconstructed images for conductivity and permittivity over a range of frequencies.
Figure 9B:
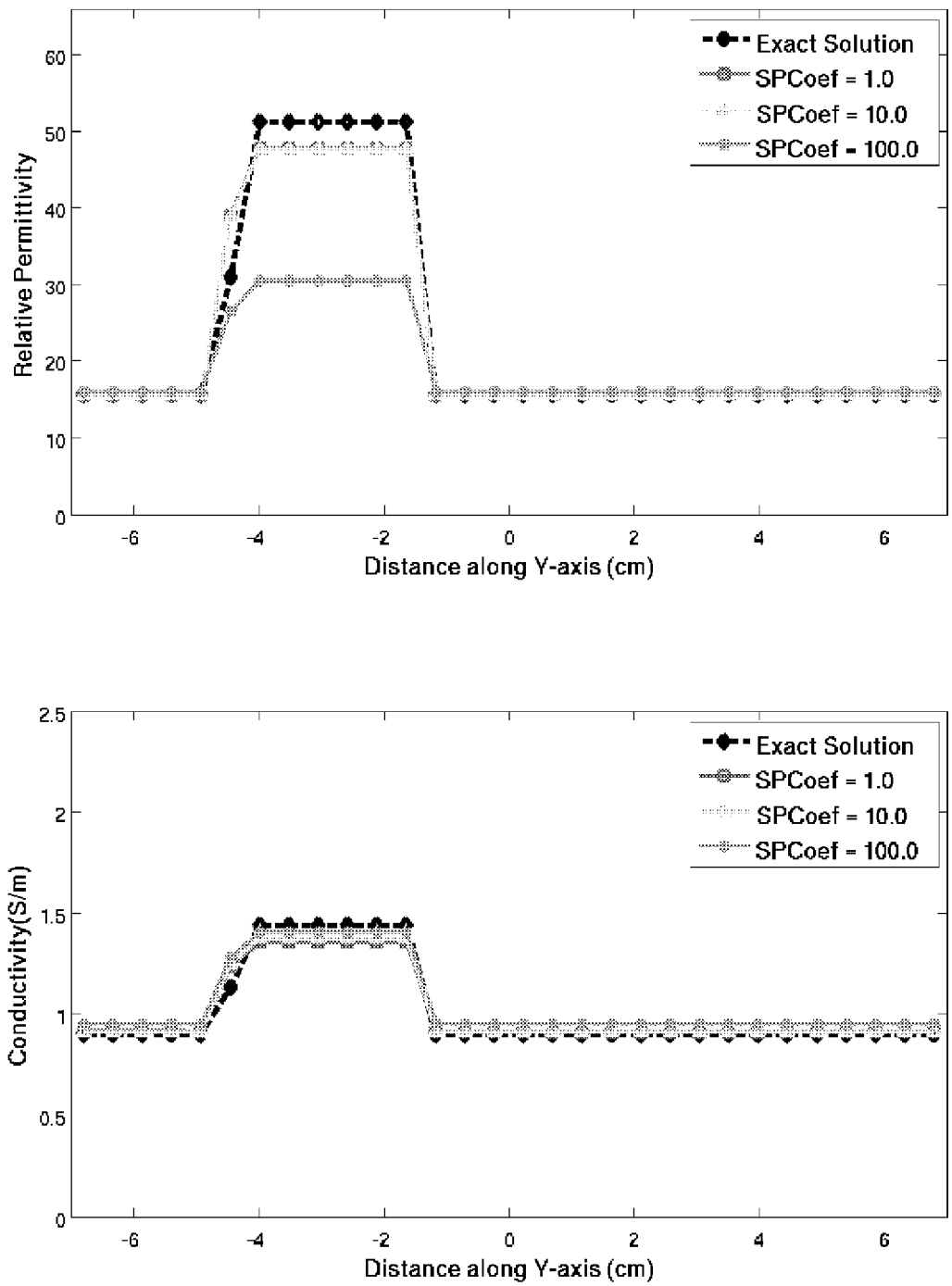
Figure 9C:
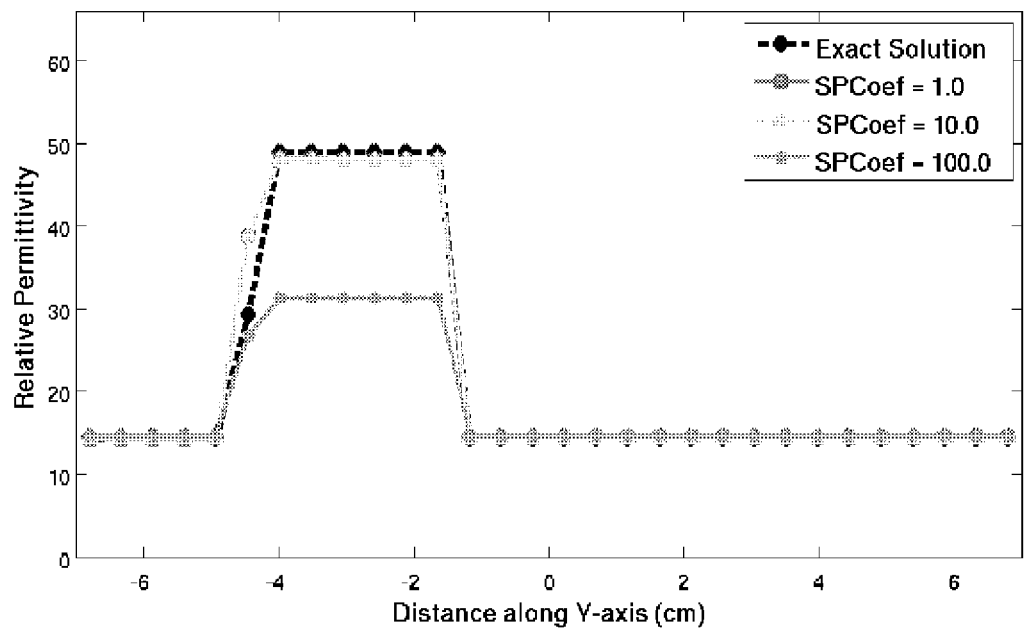
Figure 9C:
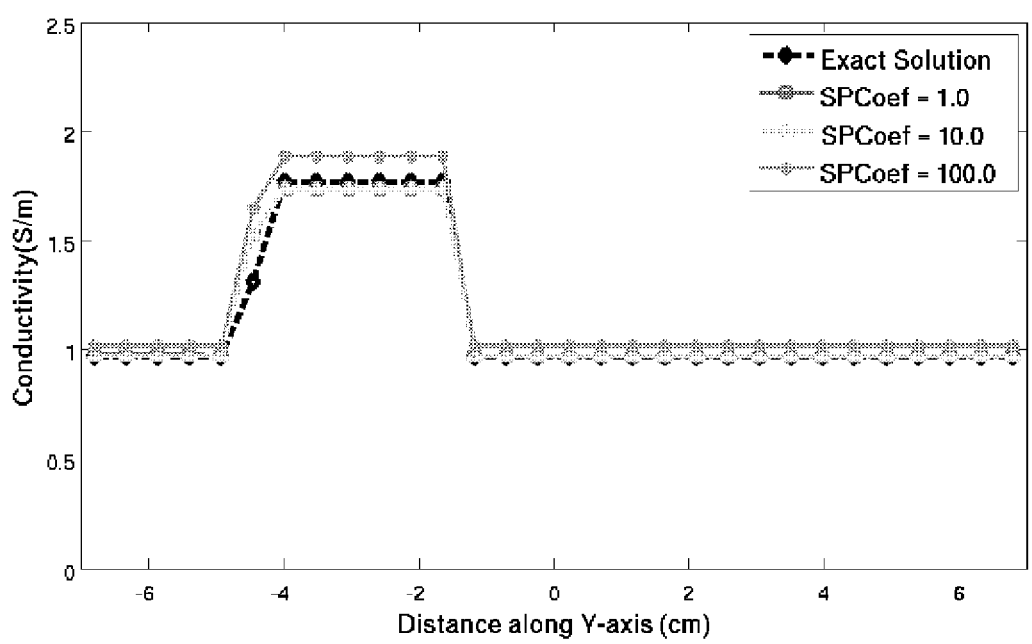
Figure 9D:
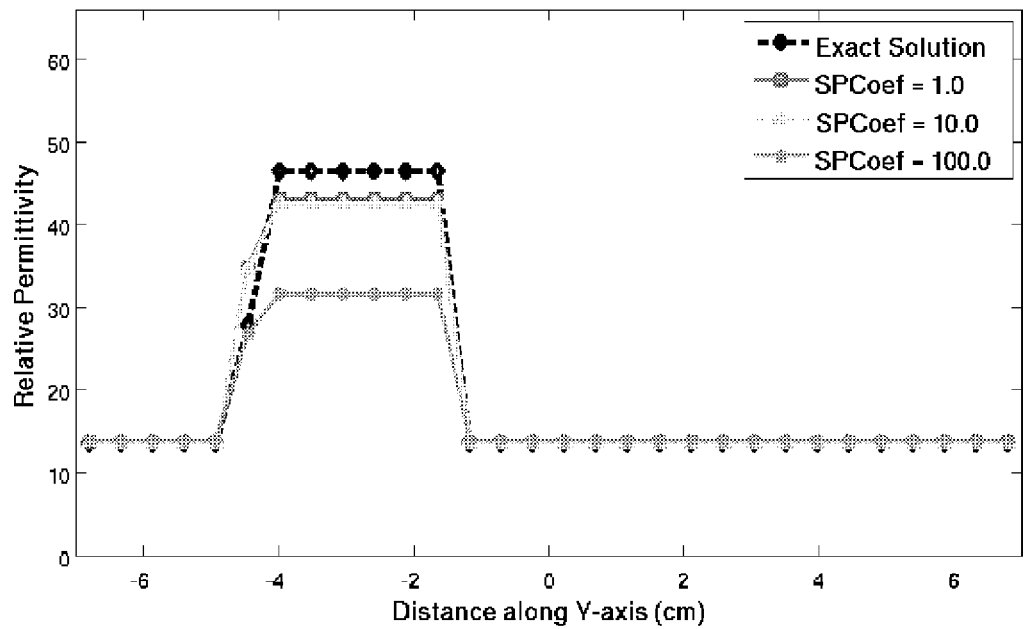
Figure 9D:
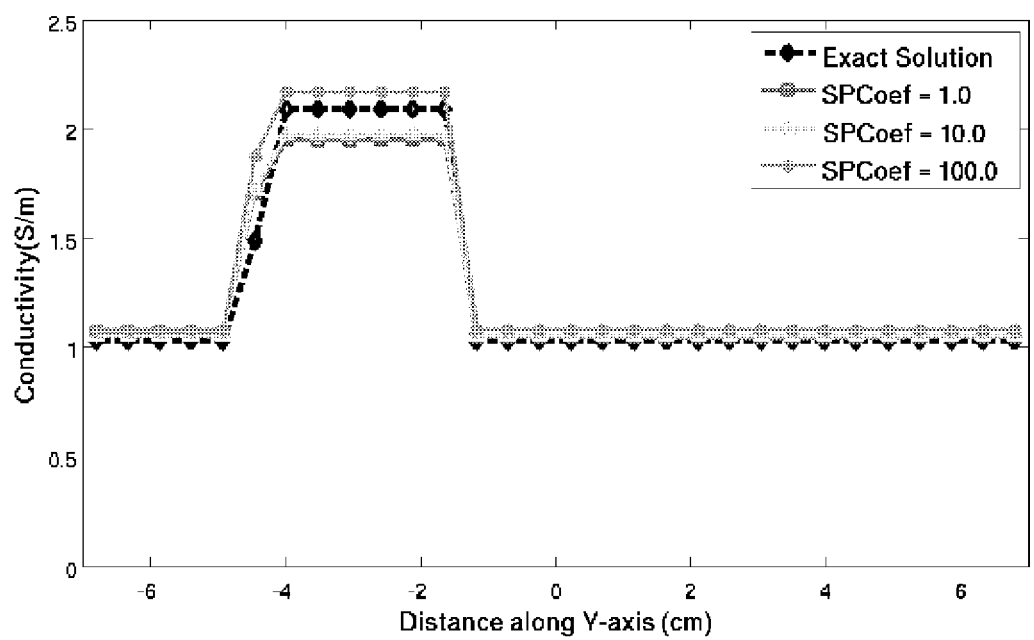

The default value of 1.0 for the weighting coefficient, λ, and the specialized soft prior mesh with 915 nodes (FIG. 3), were used to reconstruct the 1300 MHz images from the phantom experiment. FIGS. 7A-7B provide 1300 MHz reconstructed permittivity and conductivity images of the phantom experiment for the original Tikhonov algorithm of equation 6 (FIG. 7A) and the present soft prior approach of equations 4 and 7 (FIG. 7B). In both instances the inclusion 250 is recovered well. Several background artifacts appear in the original Tikhonov algorithm images (FIG. 7A), and they are more pronounced in the conductivity image. It is common in microwave tomography for the permittivity image to be of higher quality than its conductivity counterpart. However, incorporating a priori spatial information about the phantom substantially improves the quality of both the permittivity and conductivity images. Weighted permittivity and conductivity errors decrease from 0.329 and 0.302 to 0.015 and 0.045, respectively, when the spatial structure of the phantom is incorporated in the reconstruction procedure. In order to more carefully evaluate the reconstructed dielectric properties of the two approaches, constitutive parameters along the vertical transect of the y-axis are plotted in FIG. 8 and compared with the exact values.

Clearly, the soft prior regularization dramatically reduces the spatial oscillations within the background, but it also recovers the dielectric properties of the inclusion more accurately. These improvements are even more pronounced in the conductivity images. From the plots of FIG. 8 (FIG. 8A and FIG. 8B), the recovered conductivity values using the original Tikhonov algorithm are overestimated in the inclusion region. Moreover, a significant shift in location of the object occurs toward the lower edge of the imaging zone. This anomaly is eliminated when the spatial structure of the phantom is incorporated. The recovered conductivities are also notably closer to their true values using the present soft prior technique.

The soft prior coefficient $\lambda$ in equation 4 has been determined empirically. In the above description, $\lambda=1$ was used as a default, but in the following description, a more detailed study of the optimal value of $\lambda$ as a function of frequency is presented. The same experimental setup as the one previously described is used and the images are reconstructed at 1100 MHz, 1300 MHz, 1500 MHz, and 1700 MHz with the exact dielectric properties of the coupling medium and the inclusion varying over frequency, as reported in table 1 below. Table 1 illustrates actual dielectric properties of the background medium and inclusion over the range of frequencies evaluated.

TABLE 1

| Frequency (MHz) | $\epsilon_{r,bk}$ | $\sigma_{bk}$ | $\epsilon_{r,Tu}$ | $\sigma_{Tu}$ |
| --- | --- | --- | --- | --- |
| 1100 | 17.32 | 0.82 | 53.46 | 1.12 |
| 1300 | 15.61 | 0.9 | 51.16 | 1.44 |
| 1500 | 14.37 | 0.97 | 48.89 | 1.77 |
| 1700 | 13.59 | 1.03 | 46.43 | 2.09 |

A spectrum of soft prior coefficients was used for the reconstruction procedure, $\lambda=1$, 10, and 100. These values were chosen based on the testing over a wide range of trials in the simulation and phantom experiments. Lower values, such as 0.1 for $\lambda$, allowed the solution to diverge in some cases while higher values tended to suppress the recovered inclusion properties. Transects along the y-axis of the reconstructed images for $\epsilon_r$ and $\sigma$ at 1100, 1300, 1500, and 1700 MHz for the range of soft prior coefficients are shown in FIGS. 9A, 9B, 9C, and 9D, respectively. The associated weighted permittivity and conductivity errors for each image are computed and summarized in table 2 below. Table 2 illustrates weighted $\epsilon_r$ and $\sigma$ error for the phantom experiment at a range of frequencies from 1100 MHz to 1700 MHz, using three different soft prior coefficients: $\lambda=1$, 10, and 100.

TABLE 2

| Frequency (MHz) | $\mathrm{Err}_{w,\epsilon_r}$ $\lambda = 1$ | $\mathrm{Err}_{w,\sigma}$ $\lambda = 1$ | $\mathrm{Err}_{w,\epsilon_r}$ $\lambda = 10$ | $\mathrm{Err}_{w,\sigma}$ $\lambda = 10$ | $\mathrm{Err}_{w,\epsilon_r}$ $\lambda = 100$ | $\mathrm{Err}_{w,\sigma}$ $\lambda = 100$ |
| --- | --- | --- | --- | --- | --- | --- |
| 1100 | 0.019 | 0.074 | 0.026 | 0.068 | 0.201 | 0.177 |
| 1300 | 0.015 | 0.045 | 0.012 | 0.044 | 0.134 | 0.165 |
| 1500 | 0.012 | 0.011 | 0.009 | 0.016 | 0.106 | 0.150 |
| 1700 | 0.023 | 0.066 | 0.015 | 0.067 | 0.094 | 0.143 |

In general, no observable difference occurred between the reconstructed values when $\lambda=1.0$ and $\lambda=10$ were applied, and both permittivity and conductivity values of the background were recovered exactly. The plots for soft prior coefficients $\lambda=1.0$ and $\lambda=10$ overlap completely at each frequency, and the corresponding weighted errors in table 2 verify this observation. While the $\lambda=100$ reconstructions appear to estimate the inclusion conductivity values closer to the true levels, the corresponding permittivities are noticeably underestimated. This observation is also reflected in the weighted errors, which are elevated at all frequencies by approximately a factor of 10 when compared to the two lower $\lambda$ cases. These results suggest that values of $\lambda=1.0$ and $\lambda=10$ to be the optimal soft prior weighting coefficients over the present reconstruction frequency range, namely typically from 900 to 1700 MHz.

Figure 10:
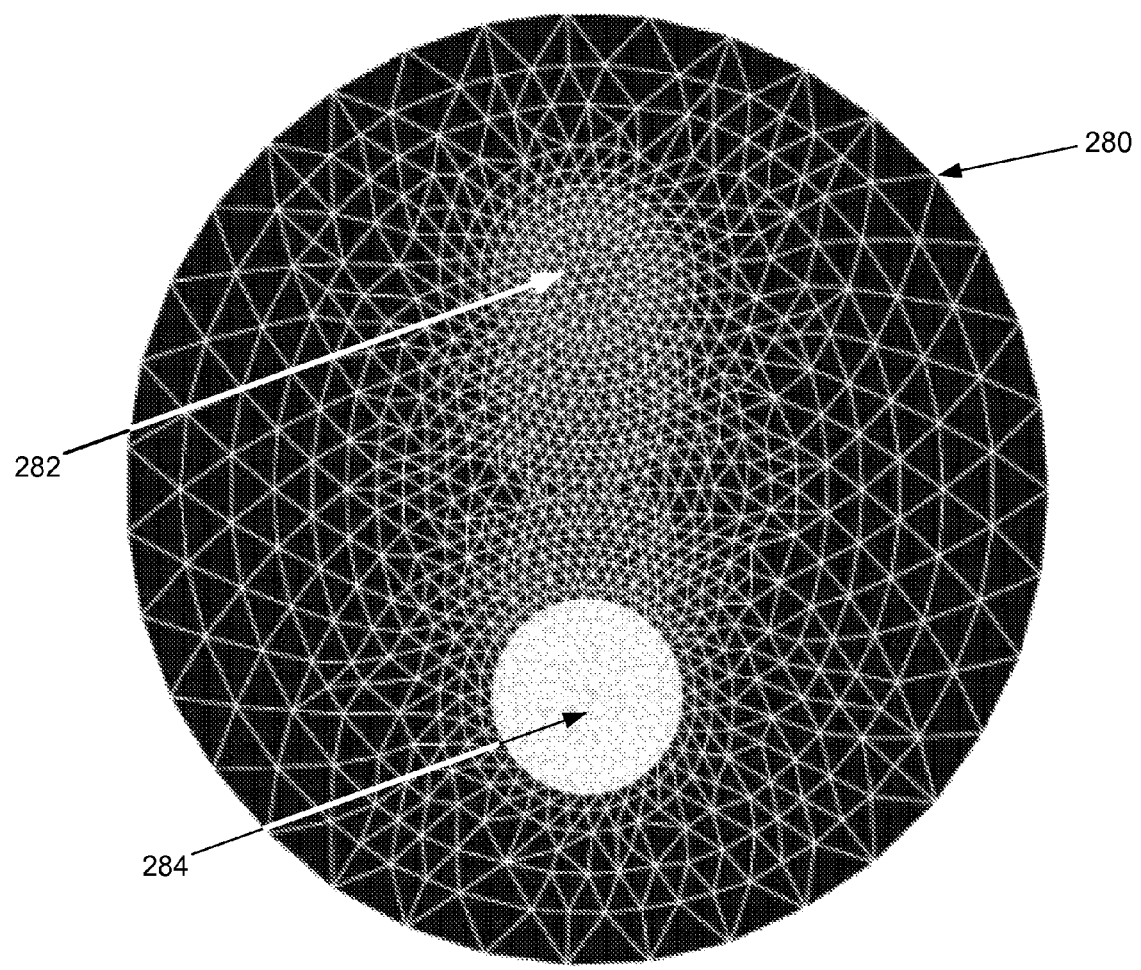
FIG. 10 is a reconstruction mesh with a false inclusion region.

In certain circumstances, prior anatomical information about tissue structure, such as from X-ray CT or MRI, may contain artifacts, and as a result, can produce erroneous regions in the reconstruction mesh. Therefore, the following provides the example of studying the sensitivity of the new soft prior regularization technique to a large false inclusion. FIG. 10 is a reconstruction mesh 280 with a false inclusion region 282 with a radius of 1.4 cm centered at (0, 3 cm) along with the previous target zone 284 with a radius of 1.4 cm centered at (0, −3 cm). The same measurement data was used as was previously used, where only a single inclusion at the lower location (0, −3 cm) existed.

Figure 11A:
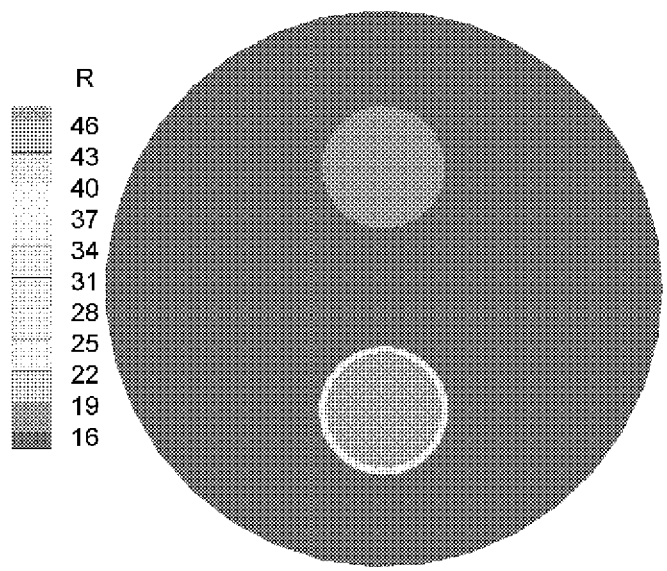
FIGS. 11A and 11B illustrate the 1300 MHz reconstructed images using $\lambda=1.0$, where
Figure 11B:
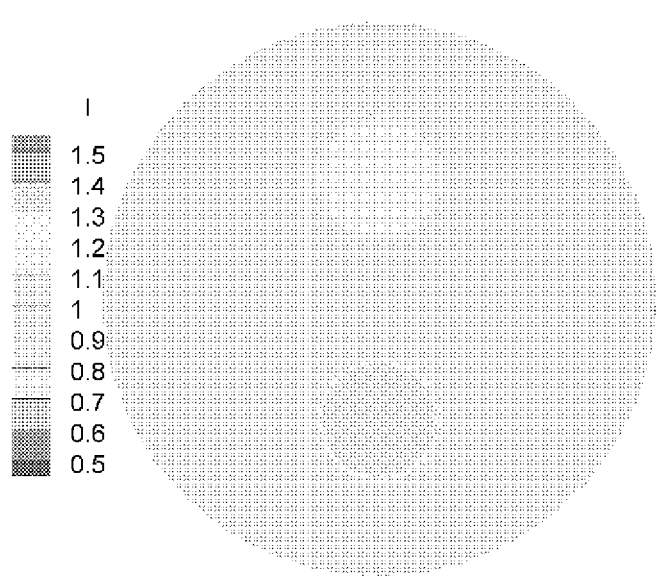

FIG. 11 illustrates the 1300 MHz reconstructed images using $\lambda=1.0$, where FIG. 11A illustrates permittivity and FIG. 11B illustrates conductivity. The false region appears as a weak increase (~6%) in the permittivity image (FIG. 11A), but with a more pronounced decrease (~−15%) in the conductivity image (FIG. 11B).

Figure 12:
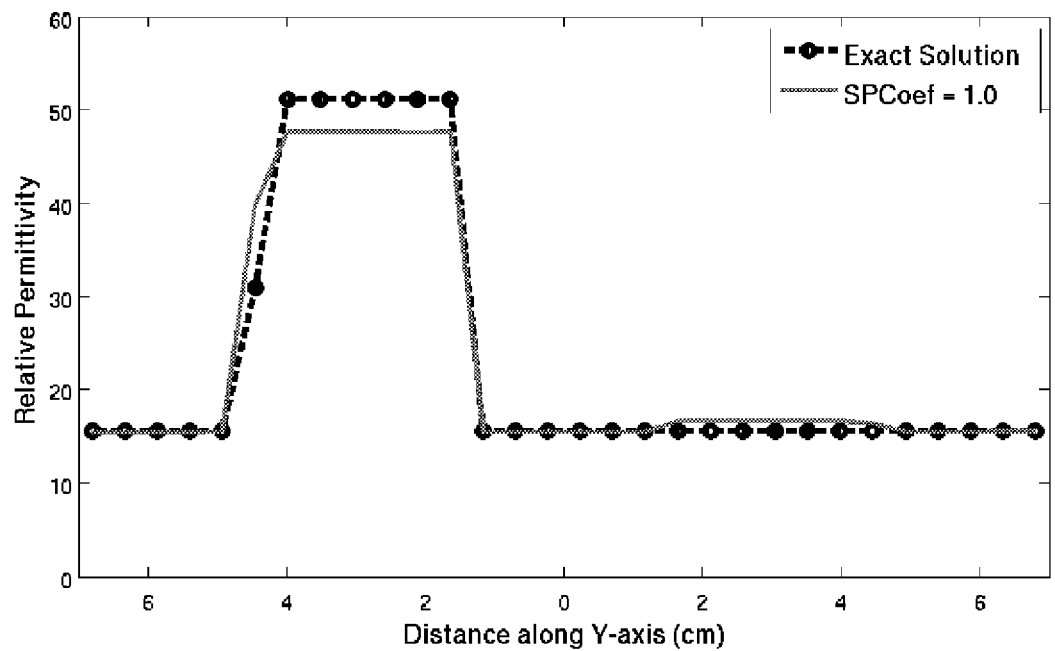
FIG. 12 illustrates 1300 MHz reconstructed permittivity and conductivity values of the phantom experiment.
Figure 12:
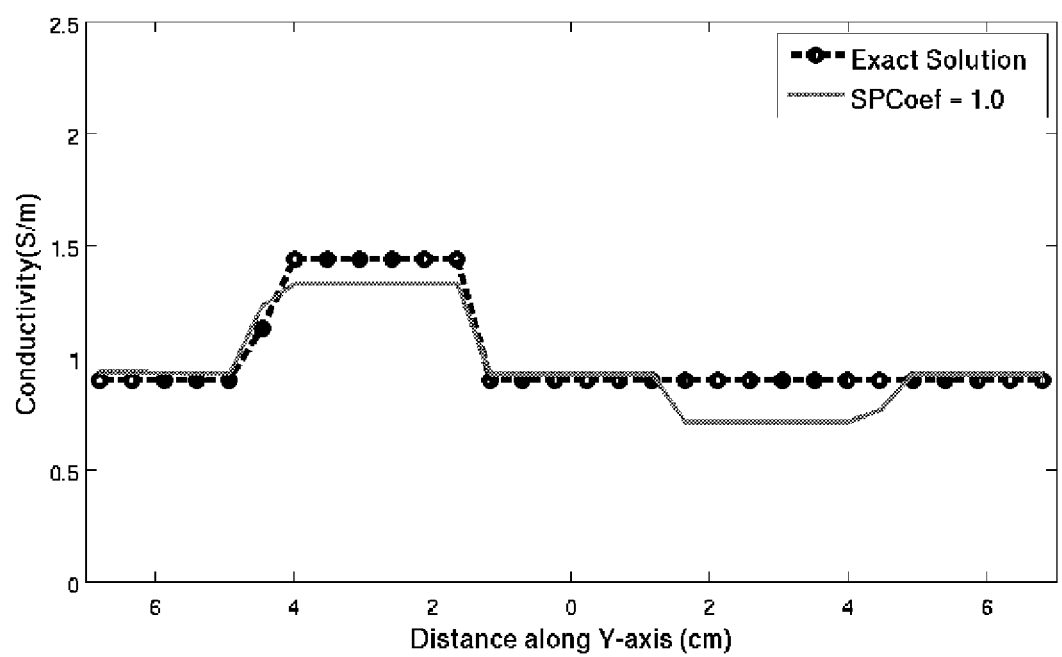

In order to analyze the sensitivity of the present soft prior algorithm to this false inclusion more precisely, transect plots through the inclusion in the permittivity and conductivity images are shown in FIG. 12. FIG. 12 illustrates 1300 MHz reconstructed permittivity (FIG. 12A) and conductivity (FIG. 12B) values of the phantom experiment using the soft prior regularization and reconstruction mesh with a false inclusion region.

Consistent with the images in FIG. 11, the permittivity values within the false inclusion region closely match the true background medium, while the conductivity is more noticeably affected by the false inclusion exhibiting lower values than the background liquid. As can be observed in FIG. 12, both $\epsilon_r$ and $\sigma$ are estimated very accurately in the true inclusion and the rest of the background, and are not significantly influenced by the presence of the false inclusion region. Weighted permittivity and conductivity errors were computed for this case, $\mathrm{err}_{w,\epsilon_r}=0.131$ and $\mathrm{err}_{w,\sigma}=0.162$, and they indicate larger errors relative to the case where the exact spatial structure of the phantom was used, but significantly lower errors than those obtained with the original Tikhonov algorithm.

Small Inclusion Phantom

Figure 13A:
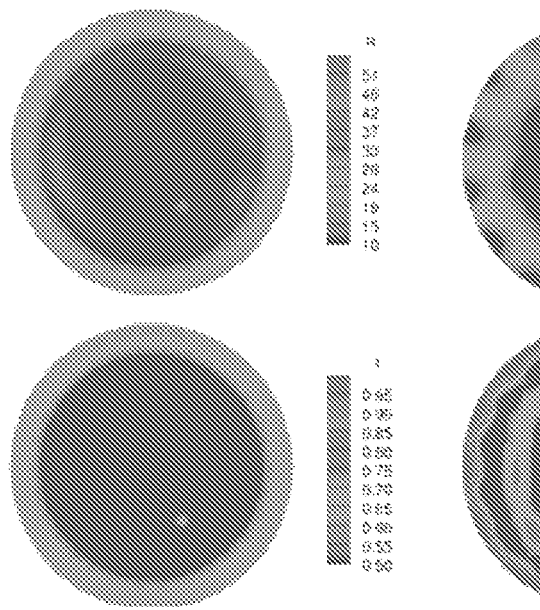
FIGS. 13A and 13B are a comparison of 900 MHz reconstructed images of the small inclusion phantom experiment.
Figure 13B:
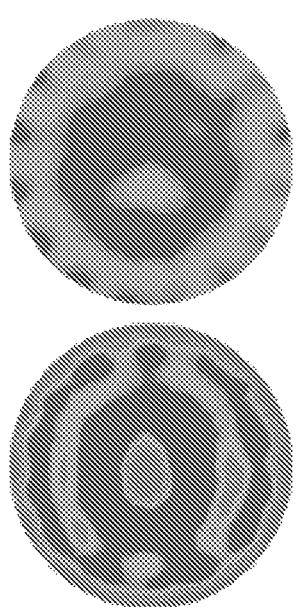

A small inclusion phantom experiment shows that inclusion that is otherwise "invisible" may be recovered with accurate contrast resolution when spatial priors are available and soft prior regularization technique is used. In this experiment, a very small cylindrical inclusion centered at (x,y)=(1.5, −2.6 cm), with a radius of only 0.25 cm and dielectric properties of $\epsilon_{r,Tu}=56.01$ and $\sigma_{Tu}=0.80$ S/m was embedded in a fatty large breast-like region centered at (x,y)=(0,0 cm), with a radius of 5.4 cm and dielectric properties of $\epsilon_{r,Tu}=9.90$ and $\sigma_{Tu}=0.39$ S/m. Both breast-like region and inclusion were then submerged into a background medium with dielectric properties of $\epsilon_{r,bk}=26.70$ and $\sigma_{bk}=0.97$ S/m. FIG. 13A represent the 900 MHz reconstructed images (permittivity on the top and conductivity on the bottom) using prior structural information of the objects. FIG. 13B likewise represent the 900 MHz reconstructed without using prior structural information of the objects, respectively.

The small inclusion is clearly detected in both permittivity and conductivity images when the present soft prior regularization method is used in the reconstruction algorithm (FIG.

13A), but does not appear in the images reconstructed with the original Tikhonov regularization approach. (FIG. 13B).

Figure 14:
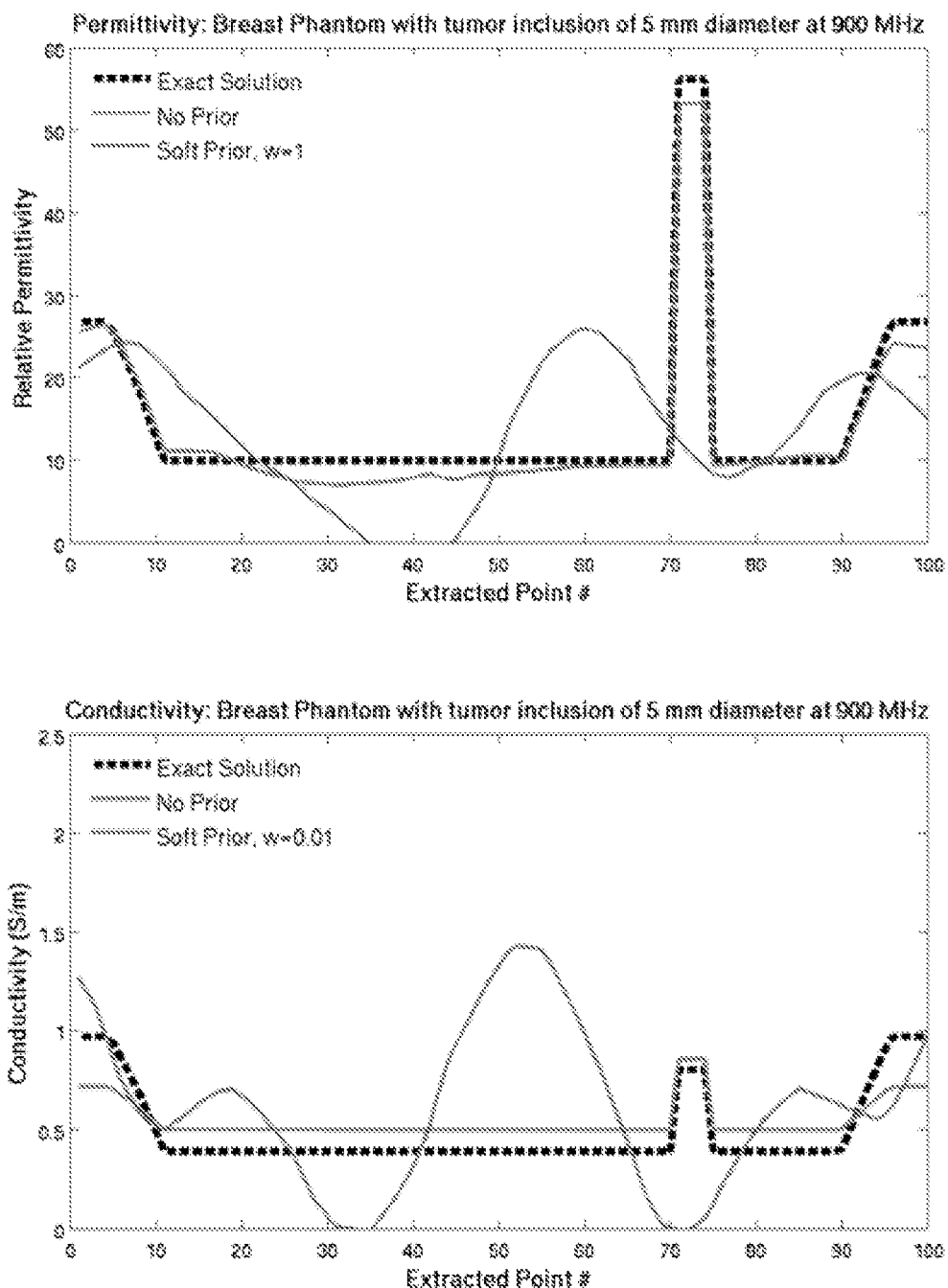
FIG. 14 is two graphs showing vertical transects for both permittivity and conductivity images for the small inclusion phantom experiment.

In order to compare the reconstructed and the true dielectric properties in the small inclusion phantom experiment more quantitatively, vertical transects for both permittivity and conductivity images along an arbitrary line passing through the inclusion are shown in FIG. 14, comparing the original Tikhonov algorithm approach to the present soft prior approach. In each figure, the plot on the top corresponds to the permittivity, while the plot on the bottom corresponds to conductivity. As illustrated in FIG. 14, the small inclusion is not detected with the original Tikhonov algorithm. However, the soft prior regularization approach of the present invention not only detects such small inclusion, but also recovers its dielectric properties very accurately with only relatively minor decrease in the permittivity image and slight increase in the conductivity one. Using the present regularization method, in the present small inclusion phantom experiment, the relative error of the reconstructed property values were less than 5% in the inclusion region. Notwithstanding, the present method clearly detected the inclusion despite its very small size.

System

Functionality of the present system and method can be implemented in software, firmware, hardware, or a combination thereof. In the first exemplary embodiment, a portion of the system is implemented in software, as an executable program, and is executed by a special or general-purpose digital computer, such as a personal computer, workstation, minicomputer, or mainframe computer. The first exemplary embodiment of a general-purpose computer architecture that can implement the present imaging system is shown in FIG. 15.

Generally, in terms of hardware architecture, as shown in FIG. 15, the computer 400 includes a processor 452, memory 460, storage device 454, and one or more input and/or output (I/O) devices 456 (or peripherals) that are communicatively coupled via a local interface 458. The local interface 458 can be, for example but not limited to, one or more buses or other wired or wireless connections, as is known in the art. The local interface 458 may have additional elements, which are omitted for simplicity, such as controllers, buffers (caches), drivers, repeaters, and receivers, to enable communications. Further, the local interface 458 may include address, control, and/or data connections to enable appropriate communications among the aforementioned components.

The processor 452 is a hardware device for executing software, particularly that stored in the memory 460. The processor 452 can be any custom made or commercially available processor, a central processing unit (CPU), an auxiliary processor among several processors associated with the computer 400, a semiconductor based microprocessor (in the form of a microchip or chip set), a macroprocessor, or generally any device for executing software instructions.

The memory 460 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 460 may incorporate electronic, magnetic, optical, and/or other types of storage media. Note that the memory 460 can have a distributed architecture, where various components are situated remote from one another, but can be accessed by the processor 452.

The software 480 in the memory 460 may include one or more separate programs, each of which comprises an ordered listing of executable instructions for implementing logical functions of the imaging system, as described above. In the example of FIG. 15, the software 480 in the memory 460 defines the imaging system functionality in accordance with the present invention, inclusive of the equations described above. In addition, the memory 460 may contain an operating system (O/S) 462. The operating system 462 essentially controls the execution of computer programs and provides scheduling, input-output control, file and data management, memory management, and communication control and related services.

The I/O devices 456 may include input devices, for example but not limited to, a keyboard, mouse, scanner, microphone, etc. Furthermore, the I/O devices 456 may also include output devices, for example but not limited to, a printer, display, etc. Finally, the I/O devices 456 may further include devices that communicate via both inputs and outputs, for instance but not limited to, a modulator/demodulator (modem; for accessing another device, system, or network), a radio frequency (RF) or other transceiver, a telephonic interface, a bridge, a router, etc.

When the imaging system is in operation, the processor 452 is configured to execute the software 480 stored within the memory 460, to communicate data to and from the memory 460, and to generally control operations of the computer 400 pursuant to the software 480. The software 480 and the O/S 462, in whole or in part, but typically the latter, are read by the processor 452, perhaps buffered within the processor 452, and then executed.

When the imaging system is implemented in software, as is shown in FIG. 15, it should be noted that the imaging system can be stored on any computer readable medium for use by or in connection with any computer related system or method. In the context of this document, a computer readable medium is an electronic, magnetic, optical, or other physical device or means that can contain or store a computer program for use by or in connection with a computer related system or method. The imaging system can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device.

In an alternative embodiment, where the imaging system is implemented in hardware, the imaging system can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

While the abovementioned first exemplary embodiment of the invention is focused on collecting and using magnetic resonance data and microwave data to identify boundaries of interest in soft tissue, in accordance with the second exemplary embodiment of the invention, the present system and method may also be applied to identify boundaries of interest in a rigid structure. An example of such a rigid structure may be, for example, but not limited to, bone. For a rigid structure, MR imaging information and microwave imaging information may be gathered separately. As an example, a patient may have MR imaging of the heel of their foot performed at a different time as microwave imaging of the heel of their foot, as long as the foot is positioned in the same manner for both the MR and microwave imaging processes. Imaging of a rigid structure at different times is possible due to rigid structures not being deformable, thereby allowing for the same alignment to be performed for both MR imaging and microwave imaging, while performed at different times. Under the above example, the foot may be held in a fixed position with a fixture or appliance, such as a form fitting boot, as the subject is transported between the MR imaging equipment and the microwave imaging equipment.

Since the heel is a rigid structure, the spatial information gathered during MR imaging may be combined with the separately gathered microwave data via the image reconstruction process described above to produce soft prior images that include quite homogeneous property distributions within each separately segmented region.

Similar to the soft tissue embodiment, the spatial information resulting from gathering MR imaging information is used by the computer to create a customized uniform mesh. Two dimensional image reconstruction, as described above, may then be performed using the spatial information resulting from gathering MR imaging information and using the microwave gathered information.

While the abovementioned describes an embodiment for providing two-dimensional imaging, it should be noted that, in accordance with an alternative embodiment of the invention, three-dimensional imaging may be provided for by the present system and method. For three-dimensional imaging, multiple MR imaging slices are taken of the sample under examination. Two-dimensional processing of each of the imaged slices is then performed so as to gather spatial information for each of the MR imaging slices. A three-dimensional mesh is then created from the gathered spatial information. There are numerous commercial 3D tetrahedral mesh generators. All fall under the same premise that if you provide the outer geometry with some internal structure information (usually a series of coordinates—or an equation that can describe a standard geometrical shape like a sphere), a mesh can be generated automatically.

Unlike the triangles of the two-dimensional mesh, nodes of the three-dimensional mesh are separated by tetrahedrons. An example of three-dimensional tomographic imaging is provided by pending patent application publication number 20060241410, entitled "Microwave Imaging System and Processes, and Associated Software Products", which is incorporated by reference in its entirety.

In accordance with another alternative embodiment of the invention, there may be instances where the geometry of an object being imaged is known ahead of time without the knowledge of MR or any other imaging modality. As an example, if a test tube filled with a liquid were imaged, one would almost certainly know the location, size and shape of that test tube. In this situation, one could easily make a mesh from the prior knowledge of the size and location of the test tube and then follow the rest of the soft prior imaging steps described above to make an image.

This could have important applications. For instance, the above-mentioned technique may be used to image bone samples and test whether the dielectric properties of the samples change as there is a reduction in mineralization of the samples through successive acid treatments. In addition, it could be used in a screening setting to test liquid containers to see if the containers have explosive liquids inside. Examples of techniques that were previously provided to detect explosive liquids include issued U.S. Pat. No. 7,319,212, entitled, "Non-invasive microwave analysis systems" and U.S. Pat. No. 7,164,105, entitled "Non-invasive microwave analysis systems," both of which are incorporated herein by reference in their entireties. While these earlier patents described how one could detect explosive liquids, the present soft prior technique certainly improves the technique. As can be seen, this technique could be used for both medical and non-medical applications.

Similarly to the explosive liquid detection embodiment described above, the present invention could be used to non-invasively test for quality and contamination of a beverage or food. For instance, one might be able to test if a wine had changed to vinegar, or if a stick of butter had gone rancid. In these cases, one could easily know the geometry of each object and by utilizing its geometry described by a set of spatial coordinates, one could generate a mesh for use in the soft prior-based algorithm. In these alternative applications, it is probable to use either the 2D algorithm or a 3D algorithm.

It should be emphasized that the above-described embodiments of the present invention are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

We claim:

1. A method for use of spatial resolution data and microwave data to identify region boundaries of interest in soft tissue, wherein the method comprises the steps of:
   simultaneously gathering spatial resolution data and microwave data from the soft tissue;
   creating a customized mesh segmented into multiple sub-zones from spatial information resulting from the gathered spatial resolution data; and
   performing image reconstruction using spatial information resulting from the gathered spatial resolution data and gathered microwave data using soft prior regularization, further comprising the steps of:
   identifying regions having the same or similar dielectric properties;
   penalizing a variation within the regions identified to have the same or similar dielectric properties; and
   restricting smoothing across a boundary shared by a first region within the gathered spatial resolution data identified to have a first set of dielectric properties and a second region within the gathered spatial resolution data identified to have a second set of dielectric properties.

2. The method of claim 1, further comprising the step of identifying boundaries between regions within the spatial resolution data.

3. The method of claim 1, further comprising the steps of:
   generating a permittivity image from the gathered microwave data; and
   generating a conductivity image from the gathered microwave data.

4. The method of claim 1, wherein the gathered spatial resolution data is selected from the group consisting of a magnetic resonance image and an X-ray computed tomography image.

5. The method of claim 1, wherein the performed image reconstruction is selected from the group consisting of two-dimensional image reconstruction and three-dimensional image reconstruction.

6. A method for use of spatial resolution data and microwave data to identify region boundaries of interest in a rigid structure, wherein the method comprises the steps of:

gathering spatial resolution data from the rigid structure;
gathering microwave data from the rigid structure;
creating a customized mesh segmented into multiple subzones from spatial information resulting from the gathered spatial resolution data; and
performing image reconstruction using spatial information resulting from the gathered spatial resolution data and the gathered microwave data using soft prior regularization, further comprising the steps of:
  identifying regions having the same or similar dielectric properties;
  penalizing a variation within the regions identified to have the same or similar dielectric properties; and
  restricting smoothing across a boundary shared by a first region within the gathered spatial resolution data identified to have a first set of dielectric properties and a second region within the gathered spatial resolution data identified to have a second set of dielectric properties.

7. The method of claim 6, further comprising the step of identifying boundaries between regions within the spatial resolution data.

8. The method of claim 6, wherein the gathered spatial resolution data is selected from the group consisting of a magnetic resonance image and an X-ray computed tomography image.

9. The method of claim 6, wherein the performed image reconstruction is selected from the group consisting of a two-dimensional image reconstruction and a three-dimensional image reconstruction.

10. In a system for use of spatial resolution data and microwave data to identify boundaries of interest in tissue, a non-transitory machine readable medium comprising instructions to perform the steps of:
  gathering spatial resolution data and microwave data from the tissue;
  creating a customized mesh segmented into multiple subzones from spatial information resulting from the gathered spatial resolution data; and
  performing image reconstruction using spatial information resulting from the gathered spatial resolution data and gathered microwave data using soft prior regularization, further comprising instructions to perform the steps of:
    identifying regions having the same or similar dielectric properties;
    penalizing a variation within the regions identified to have the same or similar dielectric properties; and
    restricting smoothing across a boundary shared by a first region within the gathered spatial resolution data identified to have a first set of dielectric properties and a second region within the gathered spatial resolution data identified to have a second set of dielectric properties.

11. The non-transitory machine readable medium of claim 10, further comprising instructions to perform the step of identifying boundaries between regions within the spatial resolution data.

12. The non-transitory machine readable medium of claim 10, further comprising instructions to perform the steps of:
  generating a permittivity image from the gathered microwave data; and
  generating a conductivity image from the gathered microwave data.

13. The non-transitory machine readable medium of claim 10, wherein the gathered spatial resolution data is selected from the group consisting of a magnetic resonance image and an X-ray computed tomography image.

14. The non-transitory machine readable medium of claim 10, wherein the performed image reconstruction is selected from the group consisting of two-dimensional image reconstruction and three-dimensional image reconstruction.

15. The non-transitory machine readable medium of claim 10, wherein the gathering of spatial resolution data and microwave data from the tissue is performed simultaneously.

* * * * *

UNITED STATES PATENT AND TRADEMARK OFFICE
CERTIFICATE OF CORRECTION

PATENT NO. : 8,977,340 B2  
APPLICATION NO. : 13/577788  
DATED : March 10, 2015  
INVENTOR(S) : Amir H. Golnabi, Paul Meaney and Keith Paulsen Page 1 of 1

It is certified that error appears in the above-identified patent and that said Letters Patent is hereby corrected as shown below:

On the Title Page

On page 1, at (73): Assignee's name is listed as Dartmounth College. Assignee's correct name is Dartmouth College.

Signed and Sealed this  
Seventh Day of July, 2015

Michelle K. Lee  
*Director of the United States Patent and Trademark Office*